(12) United States Patent
Isham

(10) Patent No.: US 10,782,425 B2
(45) Date of Patent: Sep. 22, 2020

(54) PSD SENSORS FOR HEAD AND NECK

(71) Applicant: AngioDynamics, Inc., Latham, NY (US)

(72) Inventor: John Isham, Houston, TX (US)

(73) Assignee: AngioDynamics, Inc., Latham, NY (US)

( * ) Notice: Subject to any disclaimer, the term of this patent is extended or adjusted under 35 U.S.C. 154(b) by 0 days.

(21) Appl. No.: 16/368,447

(22) Filed: Mar. 28, 2019

(65) Prior Publication Data

US 2019/0235095 A1    Aug. 1, 2019

Related U.S. Application Data

(63) Continuation of application No. 16/130,480, filed on Sep. 13, 2018, now abandoned.

(60) Provisional application No. 62/561,646, filed on Sep. 21, 2017.

(51) Int. Cl.
| | |
|---|---|
| *G01T 1/20* | (2006.01) |
| *G01T 1/02* | (2006.01) |
| *G01T 1/161* | (2006.01) |
| *A61N 5/06* | (2006.01) |
| *G01T 1/203* | (2006.01) |
| *A61N 5/10* | (2006.01) |

(52) U.S. Cl.
CPC .......... *G01T 1/2033* (2013.01); *A61N 5/0603* (2013.01); *A61N 5/1071* (2013.01); *G01T 1/023* (2013.01); *G01T 1/161* (2013.01); *G01T 1/201* (2013.01); *G01T 1/2002* (2013.01); *A61N 2005/0605* (2013.01); *A61N 2005/0606* (2013.01); *A61N 2005/0607* (2013.01); *A61N 2005/1059* (2013.01)

(58) Field of Classification Search
CPC .... A61N 2005/0605; A61N 2005/0606; A61N 2005/0607; A61N 5/0603; G01T 1/023; G01T 1/161; G01T 1/2002; G01T 1/201; G01T 1/2033

See application file for complete search history.

(56) References Cited

U.S. PATENT DOCUMENTS

| | | | |
|---|---|---|---|
| 2009/0105605 A1* | 4/2009 | Abreu | A61B 5/0046 600/549 |
| 2012/0029281 A1* | 2/2012 | Frassica | A61B 1/00154 600/114 |
| 2014/0198901 A1* | 7/2014 | Christoff | A61B 6/425 378/98 |
| 2015/0351637 A1* | 12/2015 | Ruppersberg | A61B 1/2275 600/474 |
| 2016/0338698 A1* | 11/2016 | Cardinale | A61B 17/064 |
| 2018/0085597 A1* | 3/2018 | Isham | A61N 5/1048 |

* cited by examiner

*Primary Examiner* — Mark R Gaworecki
(74) *Attorney, Agent, or Firm* — Peter Flora, Esq.

(57) ABSTRACT

A radio-opaque plastic scintillator detector (PSD) for use in various head and neck radiation applications is described. Bite plates, nose cones and ear cones are provided for use therewith, each having hollow tubes into which PSD cables can be inserted for real time measurement of radiation during treatment.

20 Claims, 20 Drawing Sheets

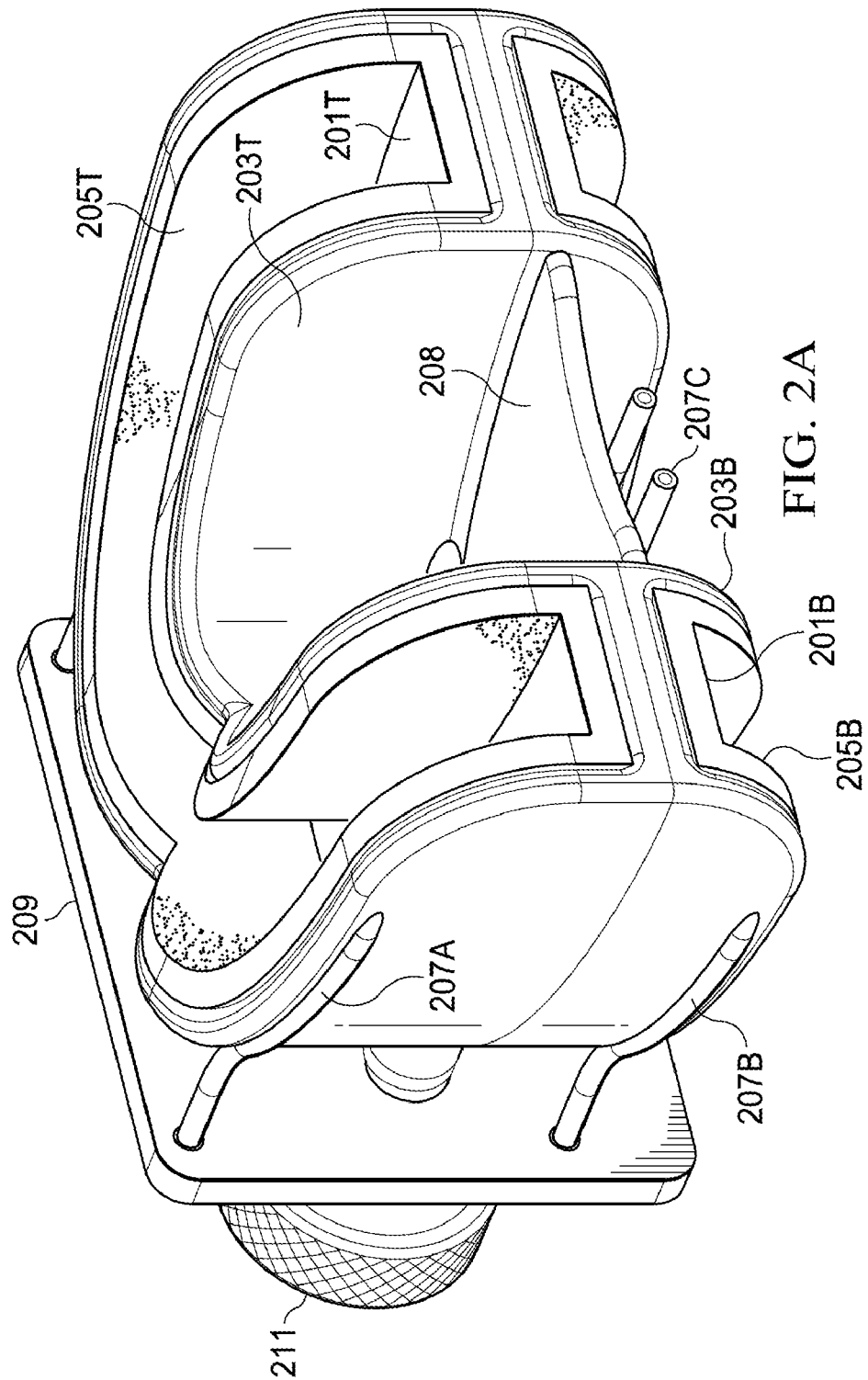

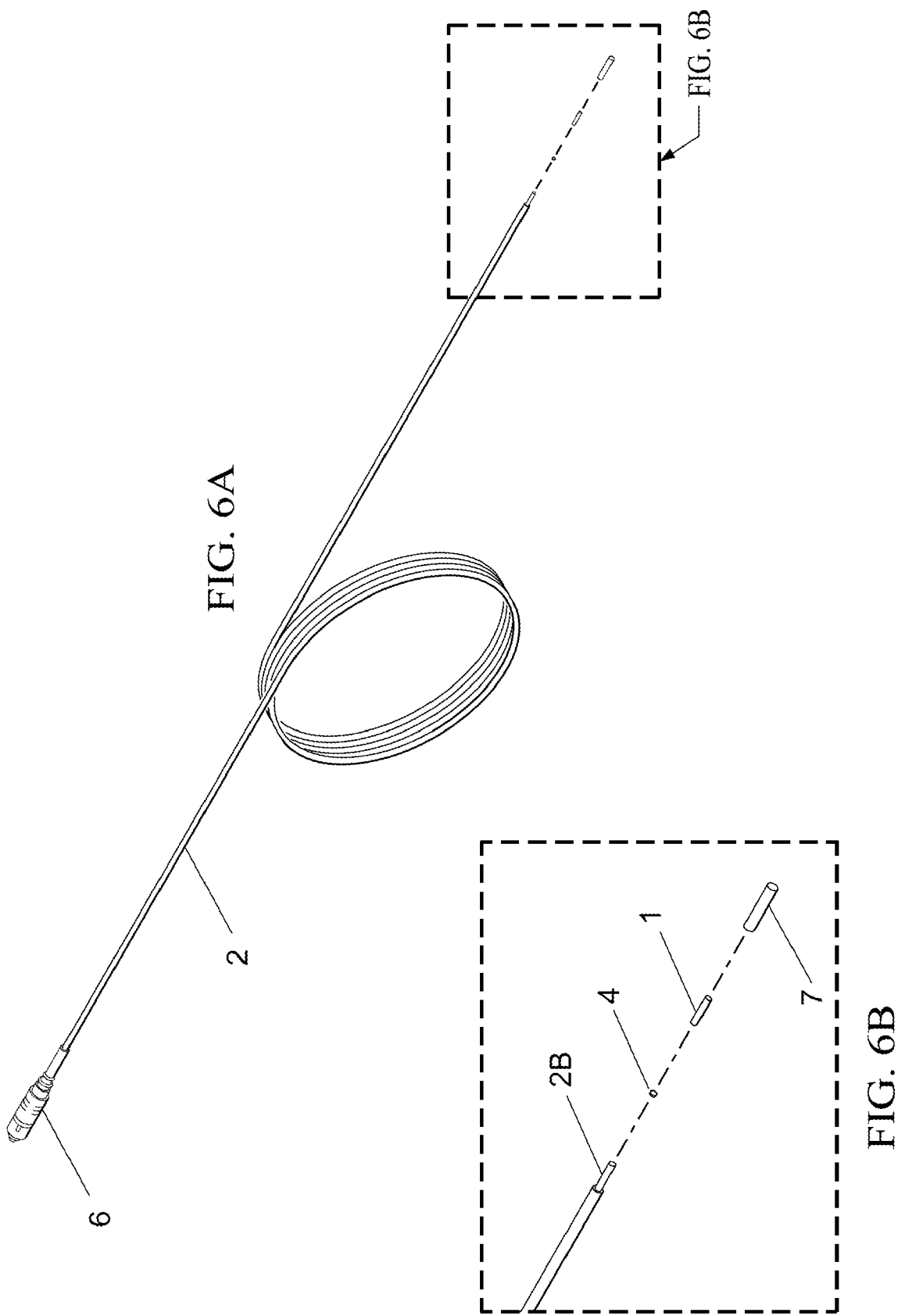

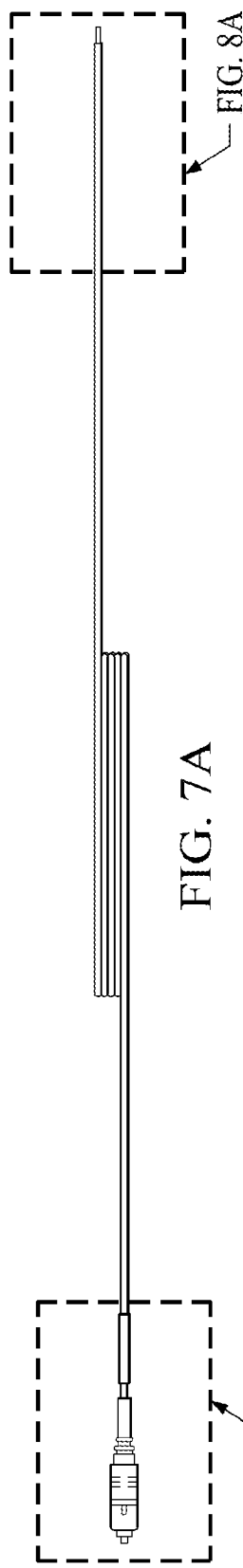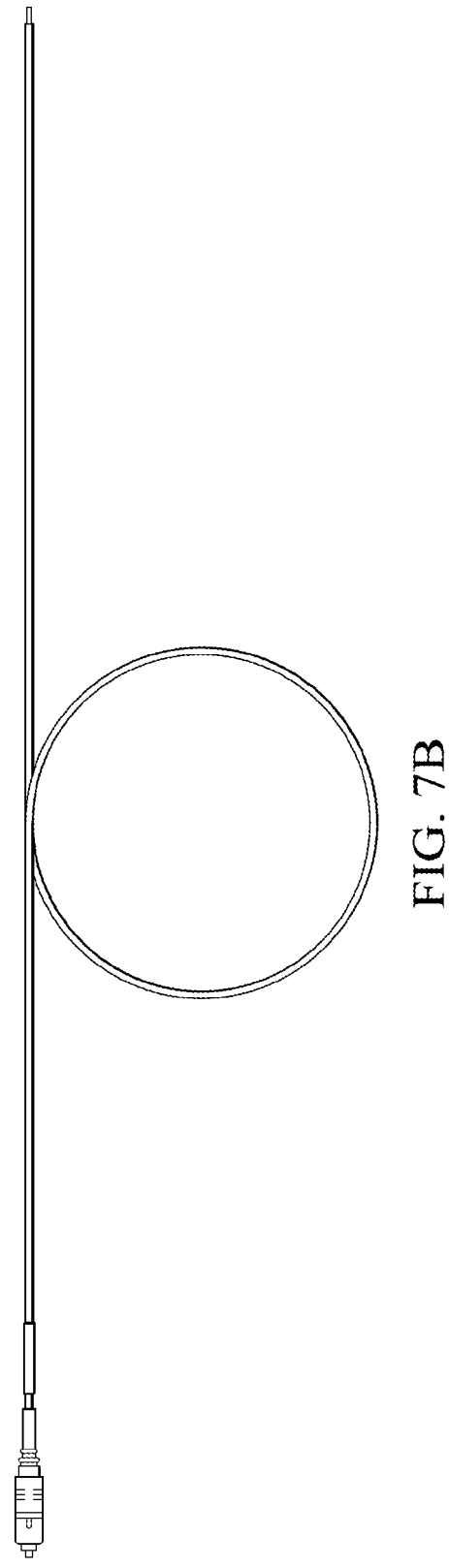

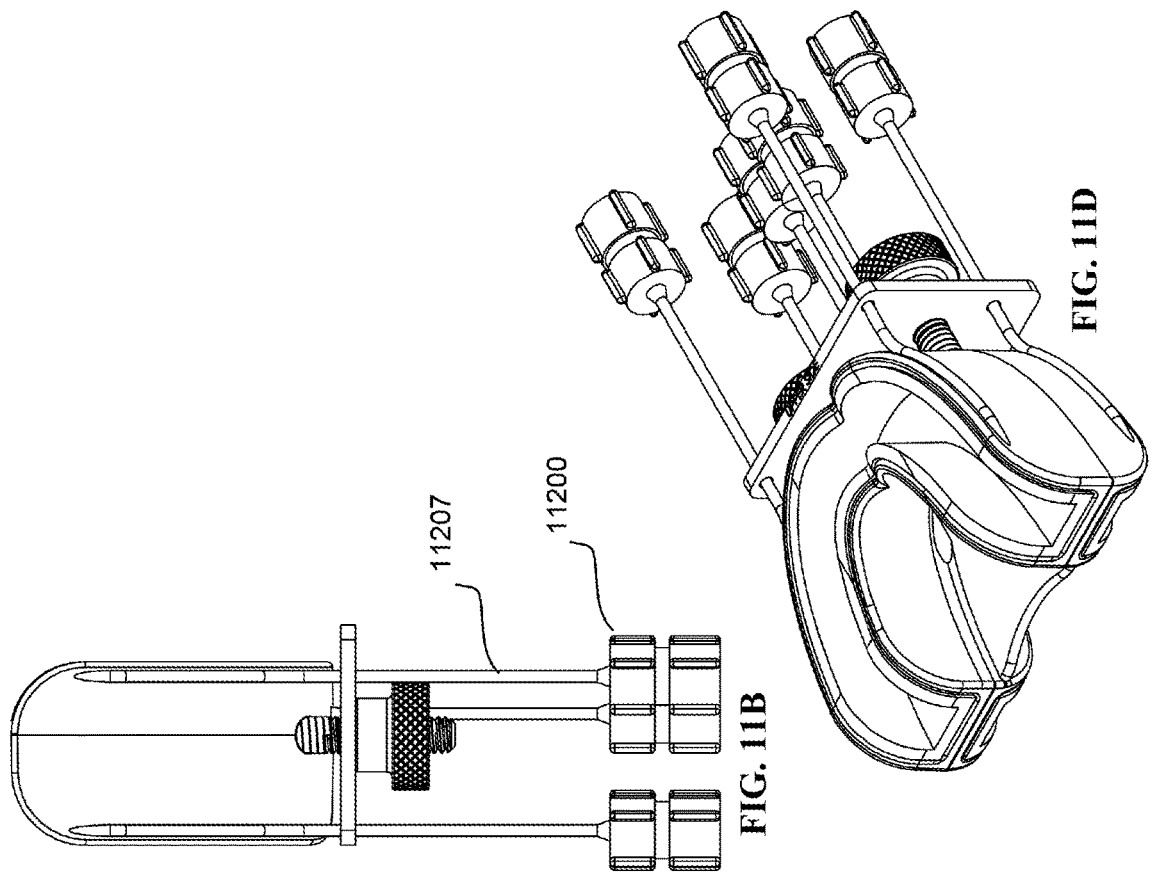
FIG. 11D
FIG. 11B
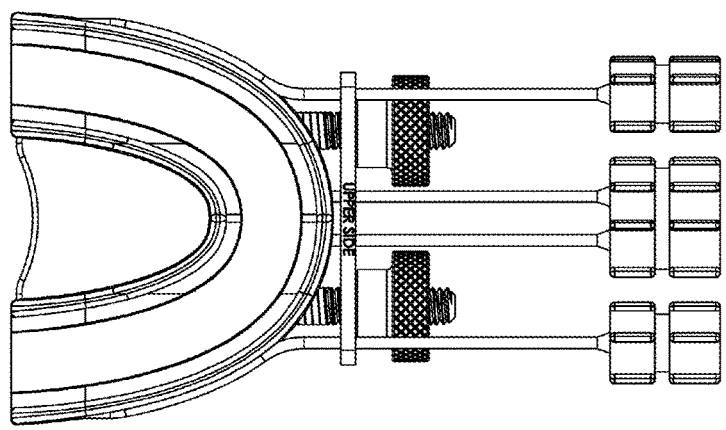
FIG. 11A
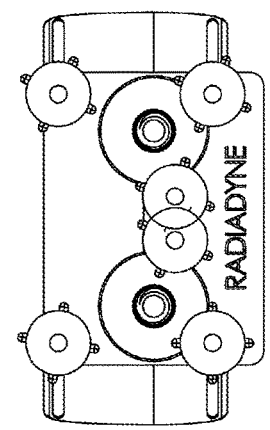
FIG. 11C

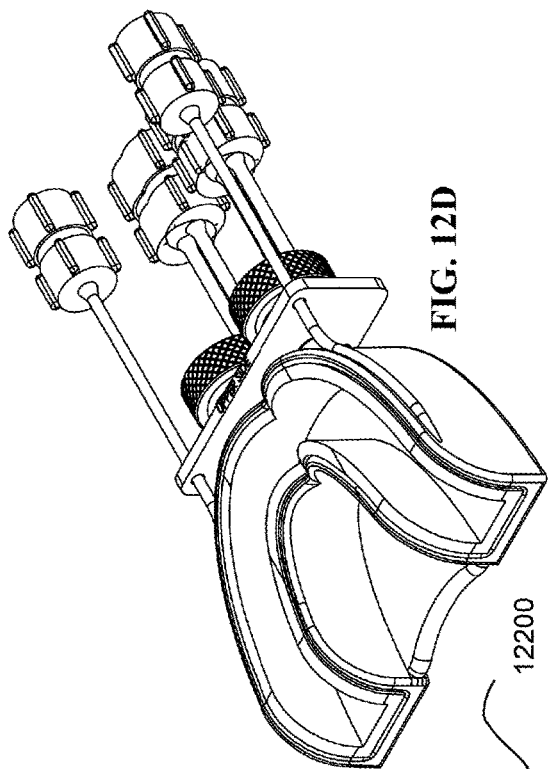
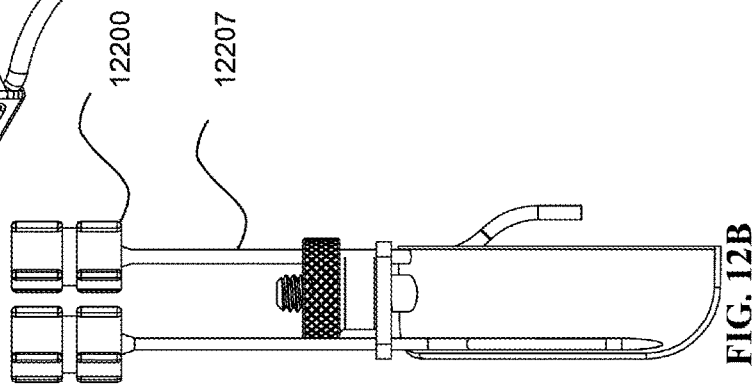
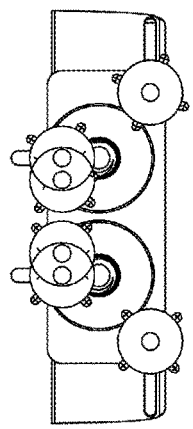
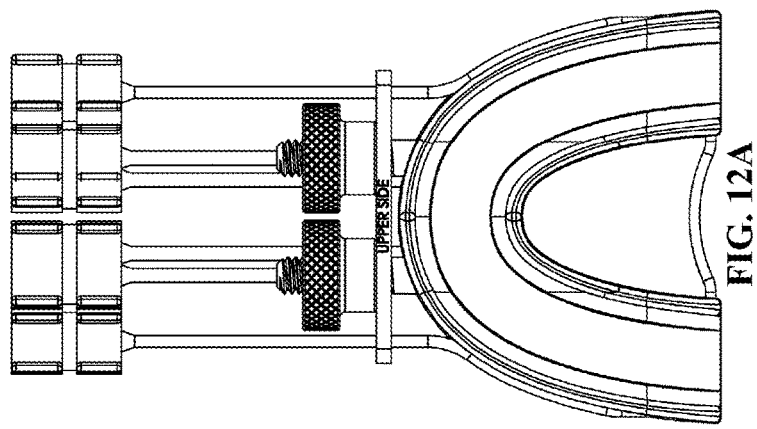
FIG. 12D
FIG. 12B
FIG. 12C
FIG. 12A 15207
15200

PSD SENSORS FOR HEAD AND NECK

PRIOR RELATED APPLICATIONS

This application claims priority to U.S. App No. 62/561,646, entitled PSD SENSORS FOR HEAD AND NECK, filed Sep. 21, 2017, and U.S. application Ser. No. 16/130,480, filed Sep. 13, 2018. Both are incorporated by reference in its entirety for all purposes.

FIELD

The invention relates to methods of making radiation sensors that are used in the head and neck region for radiation-based treatments.

BACKGROUND

A scintillator is a special material that exhibits scintillation—the property of luminescence when excited by ionizing radiation. Luminescent materials, when struck by an incoming particle, absorb its energy and scintillate, in other words they reemit the absorbed energy in the form of light.

A scintillation detector or scintillation counter is obtained when a scintillator is coupled to a light sensor such as a photomultiplier tube (PMT), charge-coupled devices (CCD), PIN photodiodes, and the like. The light sensor will absorb the light emitted by the scintillator and reemit it in the form of electrons via the photoelectric effect. The subsequent multiplication of those electrons (sometimes called photo-electrons) results in an electrical pulse that can be analyzed and provides meaningful information about the particle that originally struck the scintillator. In this way, the original amount of absorbed energy can be detected or counted.

The term "plastic scintillator" typically refers to a scintillating material where the primary fluorescent emitter, called a fluor, is suspended in a solid polymer matrix. While this combination is typically accomplished through the dissolution of the fluor prior to bulk polymerization, the fluor is sometimes associated with the polymer directly, either covalently or through coordination, as is the case with many Li6 plastic scintillators. Polyethylene naphthalate has been found to scintillate without any additives and is expected to replace existing plastic scintillators due to its higher performance and lower price.

The advantages of plastic scintillators include fairly high light output and a relatively quick signal, with a decay time between 2-4 nanoseconds. The biggest advantage of plastic scintillators, though, is their ability to be shaped, through the use of molds or other means, into almost any desired form with a high degree of durability.

In the field of medical radiation therapy, plastic scintillation detectors or "PSDs" are used to convert radiation energy into light energy, and the light photons are counted to accurately determine the radiation dose. The scintillating plastic must transfer its photons to a device that can read them, which is commonly done by coupling one or more scintillating fibers to one or more plastic optical fibers (POF). The POF is then connected to a device that can read and analyze the optical output.

A PSD or dosimeter is made of three major building blocks: the scintillating probe, a light guide and a photodetector—together called the "optical chain." The linearity between the dose and light output depends on each component in the optical chain, each stage added in the path of the optical photons leading to a decrease in efficiency. First, the visible light produced in the scintillator must travel (through internal reflection) toward the exit face of the scintillator and into the light guide (e.g. an optical fiber) (collection efficiency of about 5%). The interface between various components, e.g. scintillator to optical guide, is also a source a loss and the coupling efficiency is generally around 75-85%. Optical fibers, in particular the water-equivalent and flexible plastic types, are often used because of their enhanced light transport properties. Light attenuation in an optical fiber guide is generally less than 20% over a few meters. The output of a light guide must then be captured by a photodetector. Depending on whether the coupling to the photodetector is direct or not, passing through filters or a lens (or a combination thereof), the coupling efficiency can be as low as 5% and as high as 90%. Finally, the photodetector itself possesses an intrinsic efficiency (quantum efficiency), which can vary from 20% to 90%. The overall efficiency over the complete optical chain is thus only of a few percent and optimization of each component is important.

Manufacturing a high volume of such PSD sensor cables is difficult because an accurate and repeatable connection of the plastic scintillator fiber to the plastic optical fiber is required. The problem arises from working with small diameter optical fibers that must be constructed accurately, yet at a low cost.

U.S. Pat. Nos. 8,953,912 and 8,885,986 by Applicant describe methods of making small diameter radiation sensor cables, and 62/542,370, filed Aug. 8, 2017, entitled MANUFACTURE OF PLASTIC SCINTILLATION DOSIMETERS, describes an improved method of making small diameter PSD sensors that can also be imaged. Applicant has also provided a variety of applications for small diameter PSD use, including 62/399,407 and US20180085597, priority Sep. 25, 2016, Ser. No. 14/881,023, filed Oct. 15, 2015, 62/063,196 filed Oct. 13, 2014, Ser. No. 14/470,707, filed Aug. 27, 2014; Ser. No. 13/444,584, filed Apr. 11, 2012. US20160001094 describe a specific applications for use of small diameter PSD sensor cables. Each of the above are incorporated by reference herein in its entirety for all purposes.

This application describes yet another application for tiny PDS sensor cables—herein for use in the head and neck region.

SUMMARY

Generally speaking, the invention relates to tiny plastic scintillator detector cables, suitable for medical uses, methods of fabricating same, and various applications therefor. The tiny and inexpensive scintillator detectors are used to assess radiation dosage in real time, and provide a tremendous advance in the field, which previously lacked tiny, inexpensive detectors for use inside a body cavity at the actual location of the radiation therapy.

Herein we describe a variety of PSD containing devices for use in cavities in the head, such as oral, nasal and ear cavities. Thus, an oral device containing PSD sensors is described for intraoral use, and nasal and ear PSD containing devices are described for nasal and intra-aural use. All of the devices allow accurate dose measurements, and the oral device also functions to assist in immobilization of the jaw during treatment. The ear and nose devices can be inflatable, thus providing perfect fit for each patient, but the oral embodiment is typically solid. Methods of using same are also provided.

The device can be sold without PSD sensors or with PSD sensors as appropriate based on the cost of sensors. An integrated unit is more efficient for the user, because inserting the PSD cable into the hollow tubes provided for same takes some time and effort. However, separating the two components allows the PSD cables to be reused and is thus more cost effective in the long run. At this time, separate components are preferred.

Applications include brachytherapy, external beam radiation therapy, stereotactic radiosurgery/stereotactic radiotherapy (SRS/SRT), intensity modulated radiation therapy (IMRT), dynamical arc therapy, tomotherapy treatments, and any similar application where radiation sensing in a small area is needed. Particularly preferred applications include use in external beam radiation therapy of tumors and such.

In one embodiment, the plastic scintillator detector cable consists of a single, short length of scintillator fiber optically coupled to a suitable length of optic fiber, which has a standard data coupler or connector at the end of the cable opposite the scintillator fiber. The scintillator detector is thus at the distal end of the cable and a suitable data coupler is at the proximal end, and the entirety of the cable is enclosed in a flexible, opaque covering.

In another embodiment, the cable is hardwired directly to a photodetector, thus avoiding connector use. However, the use of the connector is preferred as it allows for quick and easy replacement of damaged cables.

In another embodiment, the cable has at least two separate, but closely juxtaposed, plastic scintillator detectors. The two detectors are parallel, but offset from one another in the longitudinal axis, so that radiation can be simultaneous assessed at two ends of a target, such as on either end of a tumor or both ends of an irradiated throat area, and the like.

In another embodiment, an additional fiber optic cable without plastic scintillator detector can be added thereto, and can serve the function of allowing the subtraction of any background signal, which can arise from the inherent dark current of the PMT or mostly Cerenkov light generated in the fibers. However, these effects are negligible for photon beams, and thus this extra cable is not needed.

Additional plastic scintillation detectors can be added if desired to assess radiation in three or more places along a longitudinal radiation axis. However, single scintillation detectors can also be used where sufficient for the application in question, e.g., where the area to be irradiated is quite small.

Where it is desired to assess radiation levels over more than one axis, e.g., with a larger radiation zone, a second plastic scintillator detector cable can be added, somewhat offset from the first cable (offset in the axis perpendicular to the cable), although this will obviously increase the overall size and cost of the device accordingly. Alternatively, two PSD sensor cables can be used.

The scintillator detector can be combined with any medical device suitable for insertion into a body cavity, such as a prostate balloon, vaginal balloon, catheter, needle, brachytherapy-applicator, surgical implements, and the like. Herein we describe devices specifically for the head and neck area.

For balloon usage, a small strip of balloon material can be welded to the outer surface thereof, and the scintillator cable threaded therethrough, thus reliably positioning the detector on the outer surface of the balloon. Alternatively, the cable can be placed inside the balloon and held with one or more spot welds and/or small strips of balloon material or other attachment means.

For solid medical devices, a small tube can be affixed thereto or be integral therewith, and the tiny cable threaded inside the small tube, or the cable can be affixed directly to the outside of the device. For example, a solid applicator can have a hole drilled therein for the PSD cable. Alternatively, a removable balloon can be provided for the applicator, such as is already described. The cable can also be threaded inside a catheter or needle, and other device used to access a body cavity. Currently preferred, we provide devices with hollow tubes therein, such that the cable is well protected during use by being safely nestled inside the small hollow tube.

The hollow tubes are sized to allow insertion of the 0.5-1 mm PSD cable, and leave a small amount of (~0.05-0.2 mm) clearance. If the device is not sold assembled with the PSD sensors, then the hollow tubes preferably protrude somewhat from the bulk of the device, and terminate in a connector that can be tightened over the PSD sensor cable once inserted, thus preventing motion of the sensor cable within the hollow tube. Any connector can be used, and we have used the Tuohy Borst adapter in our prototypes. This connector may be omitted if the sensor cables are integral with the device, but it can also be retained if sensor cables are intended to be subject to repair or replacement.

The scintillator detector cable has any suitable data connector or adaptor at the proximal end thereof, and is plugged into any existing or dedicated signal detection and computer system for collecting, analyzing and outputting the data collected by the scintillator detector. Suitable connectors include SMA, FDDI, ESCON, SMI, SCRJ, and the like, and will of course vary according to the system that is intended to be used with the scintillator detector cable. The data connectors can be single connectors, even for a dual or triple detector embodiment, but preferably a dual connector is used for the dual detector embodiment, etc., which keeps the cables neat and can prevent plugging sensors into the wrong channels.

Because the scintillator detector is quite small, novel fabrication methods were developed to allow cost effective, reliable manufacture and assembly therefore. In our first models, a special cap was used to allow the scintillator fiber to be reliably connected to the fiber optic cable. This cap is essentially tube shaped with a blind end, such that the scintillator fiber fits entirely into the blind end, and the fiber optic cable fits behind it. Thus, the hollow interior closely holds the ends of the two fibers in close juxtaposition (direct contact or "abutting") without the need for any adhesive on the ends of the two fibers, which greatly improves both sensitivity and reliability. The hollow interior is thus shaped to closely fit the naked fibers, and in many instances will have a circularly cross-section, although this can of course vary if the fiber cross section is varied.

The next step in our evolving PSD sensor technology allowed us to make a PSD sensor cable that is 0.5 mm in diameter (except for the connector) and is radiopaque for use in various imaging modalities. The method is robust and scalable, and provides a PSD sensor that can be seen in X-ray, MRI, CT and the like, allowing accurate positioning for use.

First, the scintillating fiber is dipped in a tantalum bath to provide radiopaque coating that is visible during imaging. Other radio-opaque materials could also be used, and other methods of application, such as spraying, painting, vapor deposition, and the like, could also be used. Once the coating has dried, hardened, or cured, the fiber is cut to length, as described below.

A hot knife blade can be used for cutting each fiber, thereby eliminating the need for polishing. A soldering iron set to 700° F. may be used with a fine point carbon steel blade having a thickness of 0.0235 inches (0.06 cm). Other hot knives, temperatures, and blade thicknesses are also contemplated, and it is known how to vary the temperature with the material being used. Many industrial hot-knives are available for use, and cutting blocks that function to ensure a 90° cut are also commercially available. Although a hot knife was originally preferred, other cutting methods can be substituted, including laser, water jet, diamond saw, and the like. In fact, we are now using a laser cutter as provide a very clean cut, not requiring polishing.

The optical fiber is also cut as described above, and a portion of the jacket stripped off for access and manipulation. A close fitting tube, e.g., a polyimide tube, is slid over the diameter of the optical fiber. Next, a tiny amount of optically transparent epoxy is inserted into the tube, followed by the cut piece of coated scintillating fiber. The fiber is gently coaxed into position against the optic cable, a minute amount of epoxy therebeteen. The scintillating fiber slightly sticks out of the tube when bonded in place (approximately 0.5 mm).

Preferably, the epoxy is placed on the sides of the fiber, so that when the tube is placed thereover, the fiber optic has a clean end. The same is repeated with the scintillator, thus the two fibers directly abut one another with no glue therebetween.

The final step is to dip the entire distal end of the sensor cable (up to including the distal end of the jacket of the optical fiber) in a black light-tight polymer or paint in order to prevent stray light from entering the sensor cable. Preferably, the material is a heat shrink polyester with carbon black color.

Tantalum is one of the radio-opaque materials that has the property of blocking X-rays during medical imaging, thus suitable for being used in imaging. Its bioinertness and relatively inexpensive price makes it suitable for an additional radio-opaqueness in the PSD.

Other radio-opaque materials include any heavy dense metal, such as iodine, cobalt, gold, bismuth, barium, tungsten, and compounds or alloys containing same. Barium sulfate ($BaSO_4$) was the first radiopaque material to be widely compounded in medical formulations and is the most common filler used with medical-grade polymers because it is very inexpensive at about 2$/lb. Bismuth is another such material, but is more expensive than barium at 20-30$/lb. A fine metal powder with a specific gravity of 19.35, tungsten (W) is more than twice as dense as bismuth and can provide a high attenuation coefficient at a moderate cost of 20$/lb. Barium sulphate, bismuth trioxide ($Bi_2O_3$), bismuth subcarbonate ($Bi_2O_2CO_3$) and bismuth oxychloride (BiOCl) are still commonly used in medical devices.

In addition to tantalum, radiopaque inks may also be applied to the scintillator by additional dipping. Radio opaque inks are designed for printing tags or reference points that are visible when exposed to X-ray, MRI or other fluorescing or imaging equipment. The inks are used to print adhesive skin patches or topical tags, or imprinted onto surgical devices, tools or other items requiring tracking. Currently, the preferable radiopaque inks in this application includes polyurethane-based ink with radio-opaque filler.

Alternatively, or in addition thereto, an exterior coating of heat shrinkable material can be added thereto for good strength and fit. The shrink tubing covers at least the detector end of the device up to and including at least a portion of the jacketed POF, and protects the detector, while keeping the components together in a tight bundle that remains flexible and can move in all directions. The shrink tubing can also cover most or all of the cable, but this will generally not be needed since plastic optical fibers are usually already jacketed, although the heat shrinkable tubing will also function to keep the fibers tightly bundled and thus may be of benefit.

Many suitable jacket plastics are known, and preferably are opaque plastics of low antigenicity or medical grade, although any plastic can be used and combined with an appropriate biocompatible coating. Such materials include low smoke zero halogen (LSFH), polyvinyl chloride (PVC), polyethylene (PE), polyurethane (PUR), polybutylene terephthalate (PBT), polyamide (PA), and the like.

Particularly preferred jacket materials are medical grade polyurethanes due to their lack of plasticizers and which are available in a variety of hardness, ranging from 60 Shore D to 90 Shore A. Particularly preferred are softer plastics of 70-80 Shore A and which give the cable considerably flexibility combined with sufficient strength. However, the polyurethane may need to overlay an opaque plastic, such as black PVC, unless opaque pigments are added thereto or an opaque paint is applied thereto.

By contrast, it is preferred that the detector end of the PSD is stiffer to protect the scintillating fiber. It will already be stiffer, by virtue of the guide tube used in assembly, but the overcoating of the sensor end with a tougher polymer will also help.

Also preferred are cable materials that withstand sterilization procedures, such as autoclaving, gamma irradiation or chemical treatments, although sterilization may be optional if combined with a separately sterilizable balloon that can completely contain the sensor, or if a non-sterile device is needed, e.g., for oral, aural or nasal applications.

In more detail, the invention includes any one or more of the following embodiment(s) in any combination(s) thereof:
An oral radiation sensor device, comprising:
a) a bite plate, sized and shaped to fit in a human mouth, and having a U-shaped base to contact occlusal surfaces of a patient's teeth;
b) said bite plate comprising one or more hollow tubes inside said bite plate;
c) said hollow tubes sized and shaped to accept a plastic scintillating radiation sensor;
d) said bite plate comprising an extraoral base operably connected to said bite plate and having means for connecting to a radiation mask, thereby holding said bite plate without motion during use.
An oral radiation sensor device, comprising:
a) a bite plate, sized and shaped to fit in a human mouth;
b) said bite plate having a U-shaped base to contact occlusal surfaces of a patients teeth, and outer rims to contact buccal surfaces of a patients teeth;
c) said bite plate comprising one or more hollow tubes inside said outer rims;
d) said hollow tubes sized and shaped to accept a plastic scintillating radiation sensor;
e) said bite plate comprising an extraoral base having means for connecting to a radiation mask, thereby holding said bite plate without motion during use.
An oral radiation sensor device, comprising:
a) a bite plate, sized and shaped to fit in a human mouth;
b) said bite plate having a U-shaped base to contact occlusal surfaces of a patients teeth, said U-shaped base having a lingual portion in contact with a patients tongue, and outer rims to contact buccal surfaces of said patients teeth;
c) said bite plate comprising one or more hollow tubes inside said outer rims and said lingual portion;
d) said hollow tubes sized and shaped to accept a plastic scintillating radiation sensor;

e) said bite plate comprising an extraoral base having means for connecting to a radiation mask, thereby holding said bite plate without motion during use.

An oral radiation sensor device, comprising:
a) a bite plate, sized and shaped to fit in a human mouth;
b) said bite plate having a U-shaped base to contact occlusal surfaces of a patients teeth, said U-shaped base having a lingual portion in contact with a patients tongue, and outer rims to contact buccal surfaces of said patients teeth and inner rims to contact lingual surfaces of at least a portion of said patients teeth;
c) said bite plate comprising one or more hollow tubes inside said outer rims and said inner rims and said lingual portion;
d) said hollow tubes sized and shaped to accept a plastic scintillating radiation sensor;
e) said bite plate comprising an extraoral base having means for connecting to a radiation mask, thereby holding said bite plate without motion during use.

An nasal or aural radiation sensor device, comprising:
a) a hollow cone, sized and shaped to fit in a human ear or nostril, said cone being inflatable;
b) an interior of said cone being fluidly connected to a cylinder comprising i) a lumen fluidly connected to an interior of said nose cone, and ii) one or more blind hollow tubes;
c) said blind hollow tubes sized and shaped to accept a plastic scintillating radiation sensor;
d) said lumen having a valve for controlling fluid flow into and out of said interior of said cone.

An nasal or aural radiation sensor device, comprising:
a) a compressible foam cone, sized and shaped to fit in a human ear or nostril, said cone being compressible for insertion but thereafter expanding to fit an available space;
b) said cone comprising one or more blind hollow tubes inside said cone;
c) said blind hollow tubes sized and shaped to accept a plastic scintillating radiation sensor.

An nasal or aural radiation sensor device, comprising:
a) a solid cone, sized and shaped to fit in a human ear or nostril;
b) said cone comprising one or more blind hollow tubes inside said cone;
c) said blind hollow tubes sized and shaped to accept a plastic scintillating radiation sensor.

Any device herein described, said hollow tube(s) being less than 1.5 mm in diameter.

Any device herein described, said hollow tube(s) being less than 1 mm in diameter.

Any device herein described, further comprising a plastic scintillating detector (PSD) cable inserted into each of said hollow tubes.

Any device herein described, further comprising a plastic scintillating detector (PSD) cable inserted into each of said hollow tubes, said PSD cable being less than 1 mm in diameter.

Any device herein described, said PSD cable comprising a radio-opaque marker on a distal tip thereof.

Any device herein described, wherein said radio-opaque marker is iodine, cobalt, gold, bismuth, barium, tungsten, and compounds or alloys containing same.

A method of treatment of a cancer, comprising:
a) inserting a PSD cable having a radio-opaque marker thereon into each hollow tube of a device described herein;
b) inserting said device into a patient at or near a cancerous target site and optionally inflating said device if applicable;
c) imaging said PSD cable and adjusting a position of said device as needed to position said PSD cable at said target site;
d) connecting a proximal connector of said PSD cable to a photodetector;
e) delivering radiation to said patient and measuring an amount of delivered radiation;
f) ceasing said delivery and recording said amount of delivered radiation; and
g) optionally deflating if applicable and removing said device from said patient.

A method of treatment of a cancer, comprising:
a) inserting the device described herein into a patient at or near a cancerous target site and optionally inflating said device if applicable;
b) imaging said PSD cable and adjusting a position of said device as needed to position said PSD cable at said target site;
c) connecting a proximal connector of said PSD cable to a photodetector;
d) delivering radiation to said patient and measuring an amount of delivered radiation;
e) ceasing said delivery and recording said amount of delivered radiation; and
f) optionally deflating if applicable and removing said device from said patient.

BRIEF DESCRIPTION OF THE DRAWINGS

A better understanding of the present invention can be obtained with the following detailed descriptions of the various disclosed embodiments in the drawings:

FIG. 2A shows a perspective view of a dual arch embodiment from the mouthpiece side.

FIG. 6A-B. A perspective view of a PSD sensor showing enlargement area A in FIG. 6B.

FIG. 7A-B Side and top views of a PSD sensor showing enlargement area B and C.

FIG. 11A Top view of completed dual arch mouthpiece, with extended hollow tubes ending in Tuohy Borst adaptors. FIG. 11B side view, 11C perspective view, and 11D end view of same device. The parts are otherwise the same as in FIG. 2 and only the new portions are labeled.

FIG. 12A Top view of completed single arch mouthpiece, with extended hollow tubes ending in Tuohy Borst adaptors. FIG. 12B side view, 12C perspective view, and 12D end view of same device.

FIG. 13A top view of completed earpiece, with extended hollow tube ending in Tuohy Borst adaptors. FIG. 13B perspective view of same.

DETAILED DESCRIPTION OF THE INVENTION

Figure 1A:
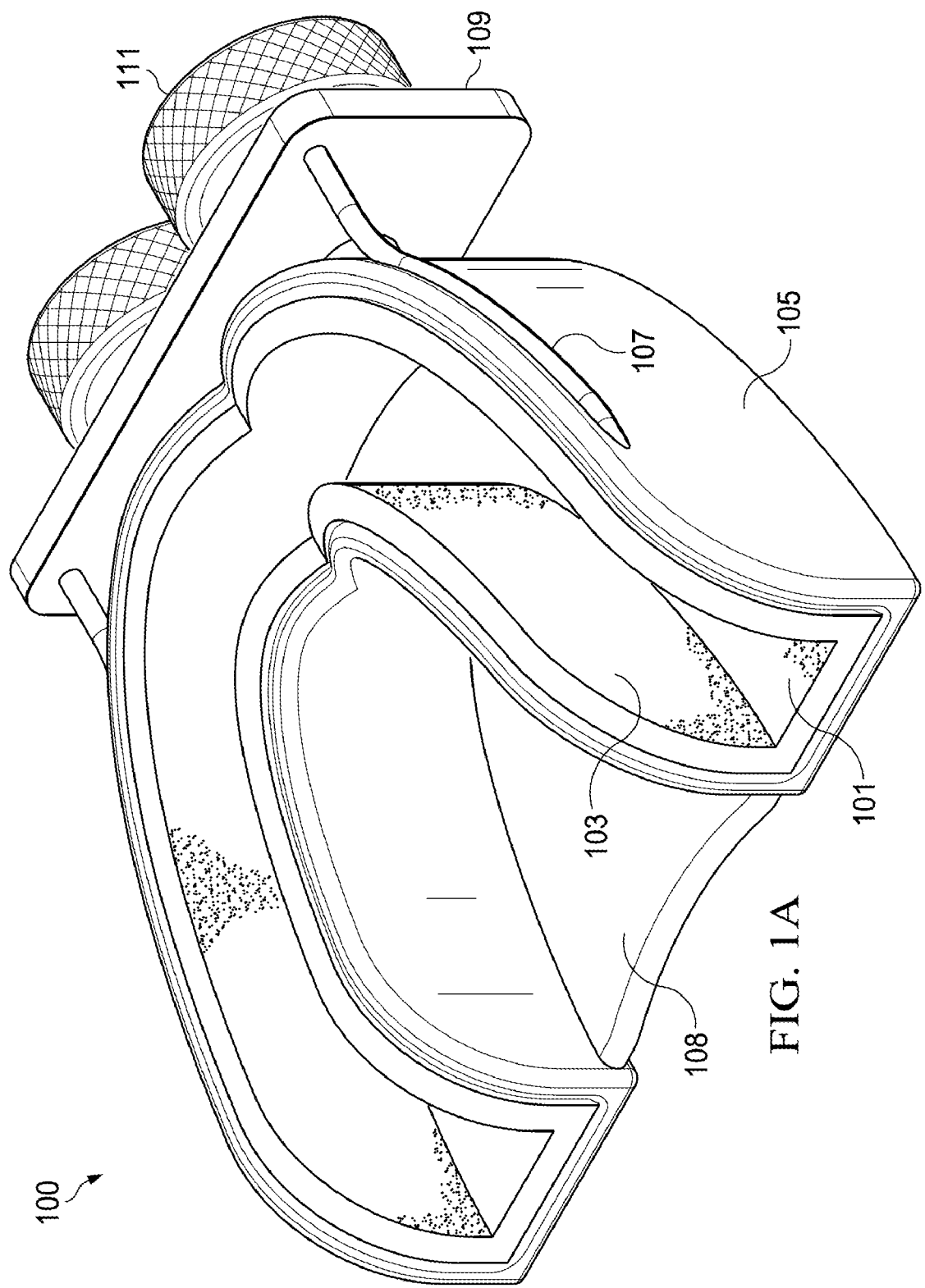
FIG. 1A shows a perspective view of an oral sensor device from the mouthpiece side.
Figure 1B:
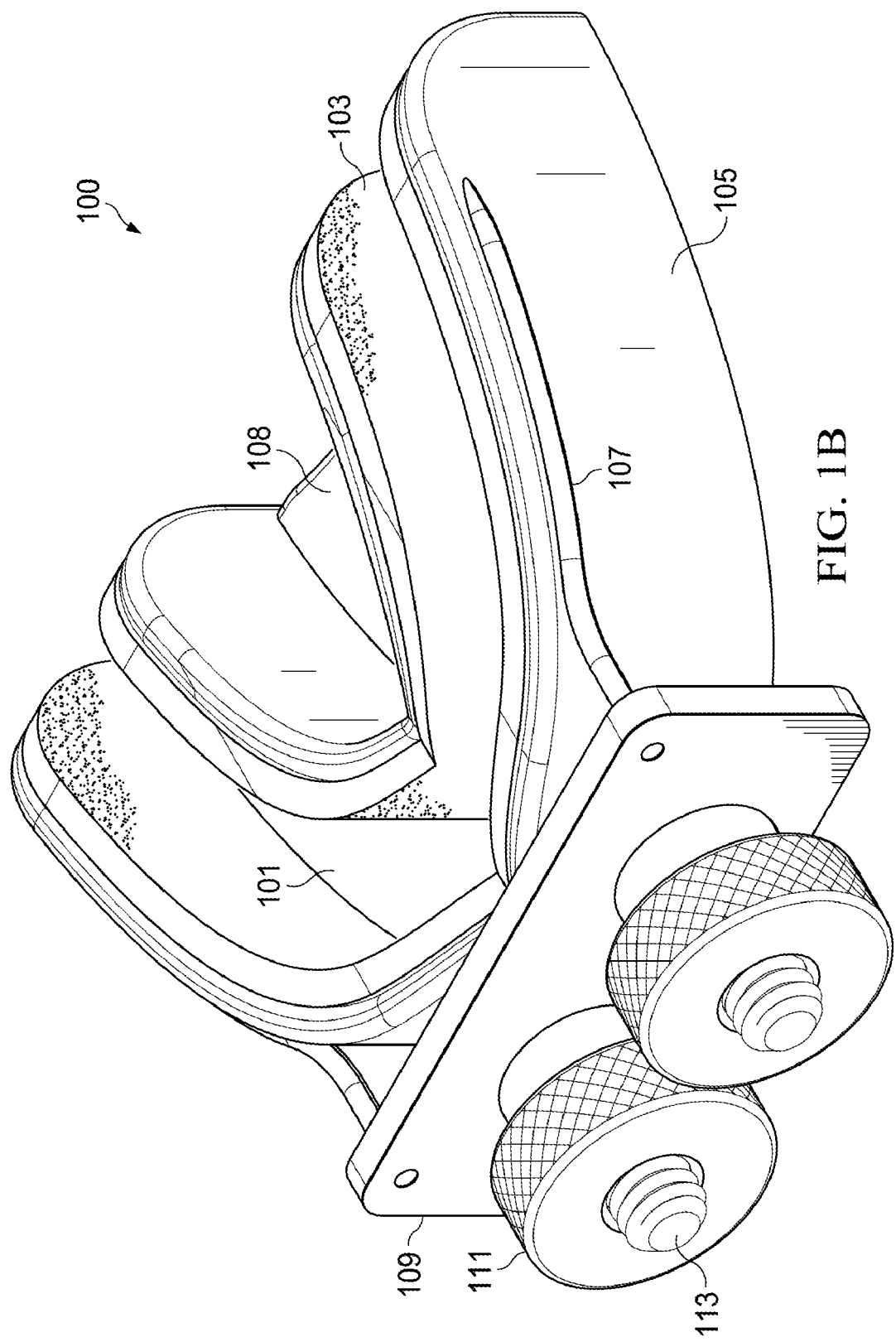
FIG. 1B shows a perspective view of FIG. 1A from the extraoral side.
Figure 1C:
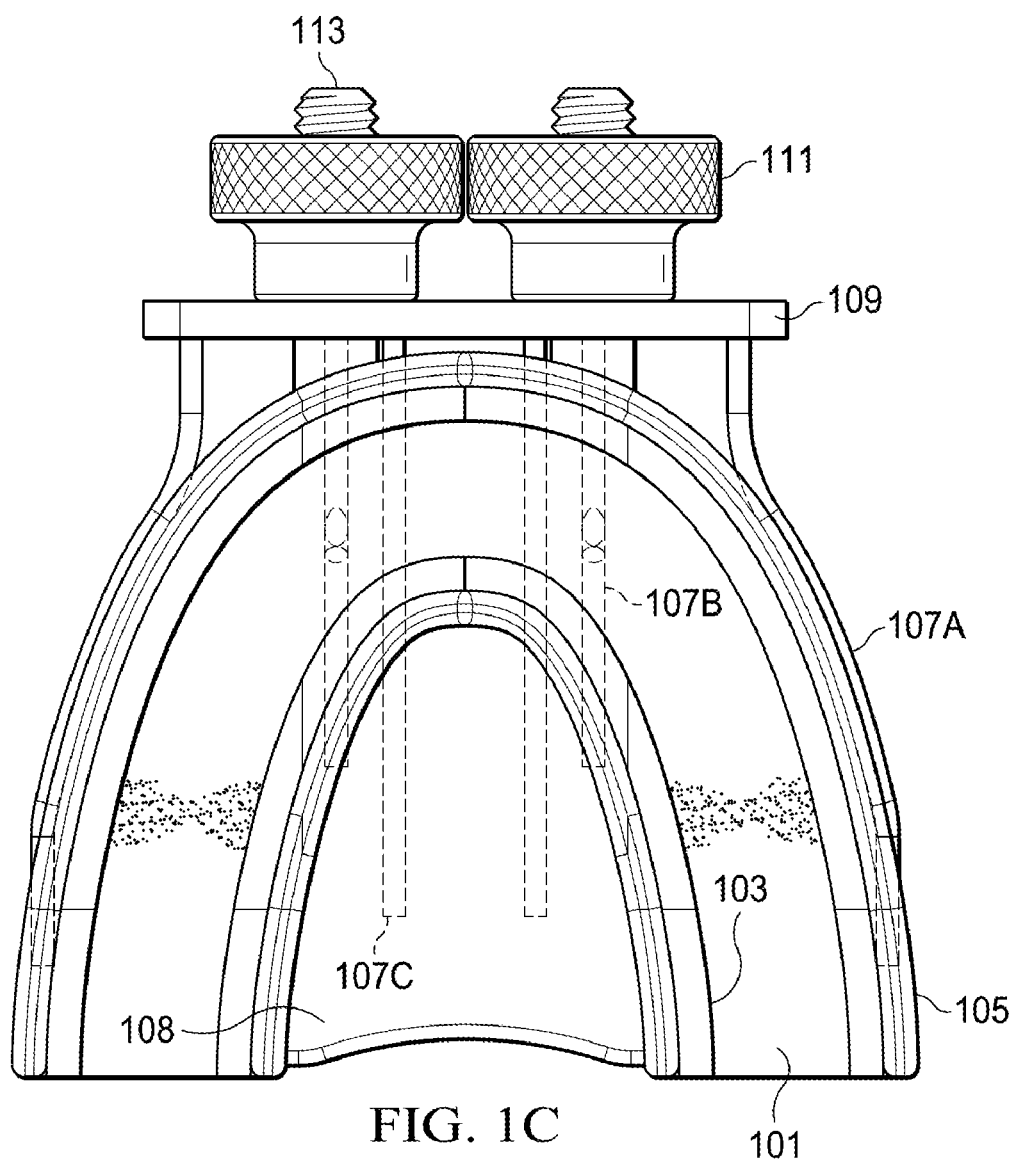
FIG. 1C is a top view of FIG. 1A.
Figure 1D:
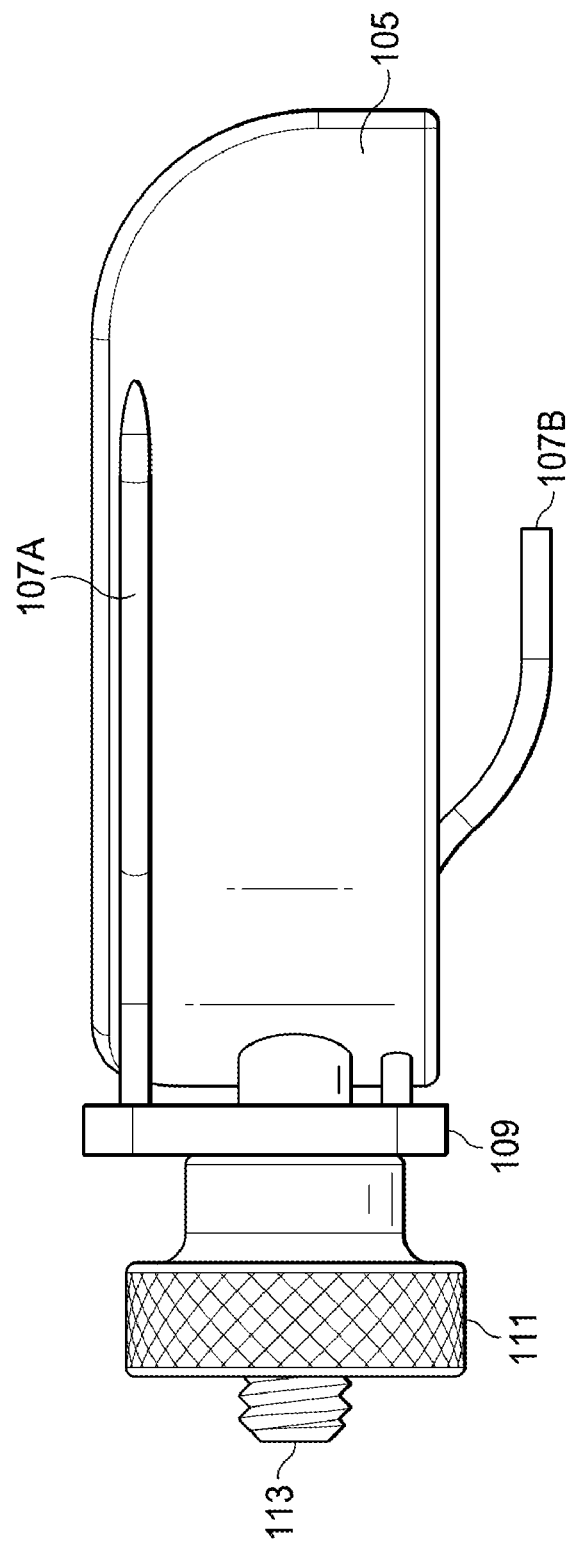
FIG. 1D is a side view of the device of FIG. 1A.

Turning to FIG. 1, a sensor-containing mouthpiece 100 that is generally U-shaped for oral use is shown in several views. FIG. 1A shows a perspective view from the mouthpiece side, 1B a perspective view from the extraoral side, 1C a top view, and 1D a side view.

The U-shaped base 101 allows contact with the occlusal surfaces of teeth, and rims or edges contact teeth. Obviously, this bite plate is sized and shaped for human use, and can be made available in a range of sizes (S, M, L, XL).

The buccal (cheek) surfaces of the mouth are contacted by outer rim 105 and the lingual surface of the teeth by inner rim 103, but either or both can be omitted depending on where sensor placement is desired. In this particular embodiment, the lingual area 108 is filled in so that sensor can be placed to measure radiation at the tongue, but this is optional, depending on which area is to be treated. The U-shaped base 101 has an extraoral component 109, that functions to provide connection to e.g., a radiation face mask, which is typically employed for external beam radiation of the head and neck. Connectors such as screw 113 and nut 111, are shown, however, other connectors are possible.

Tubes 107A, 107B and 107C provide conduits for the PSD sensors to be housed, thus allowing real-time radiation monitoring of radiation to the mouth, tongue and jaw area. The conduits continue proximally from the bite plate 101 to a connector, not shown for clarity. However, these features are seen in the diagrams of FIG. 11-15. The PSD sensor cables are inserted into these hollow tubes, again not shown for clarity, but an example is shown in FIG. 13 and the PSD sensors connect via adaptors to the photodetector. For clarity, distal and proximal are with reference to the technician, not the patient. Thus, the bite plate is distal, and the photodetector is proximal.

Placement and number of sensor conduits can vary, but here we showed paired sensors 107A on the buccal rims 105, paired sensors under the mouthpiece 107B, and paired sensors 107C inside the lingual area 108. For clarity, the sensors are not shown inside these tubes 107, but they are small cables of 0.5-1 mm in diameter, ending in a PSD sensor, as described previously.

Figure 1E:
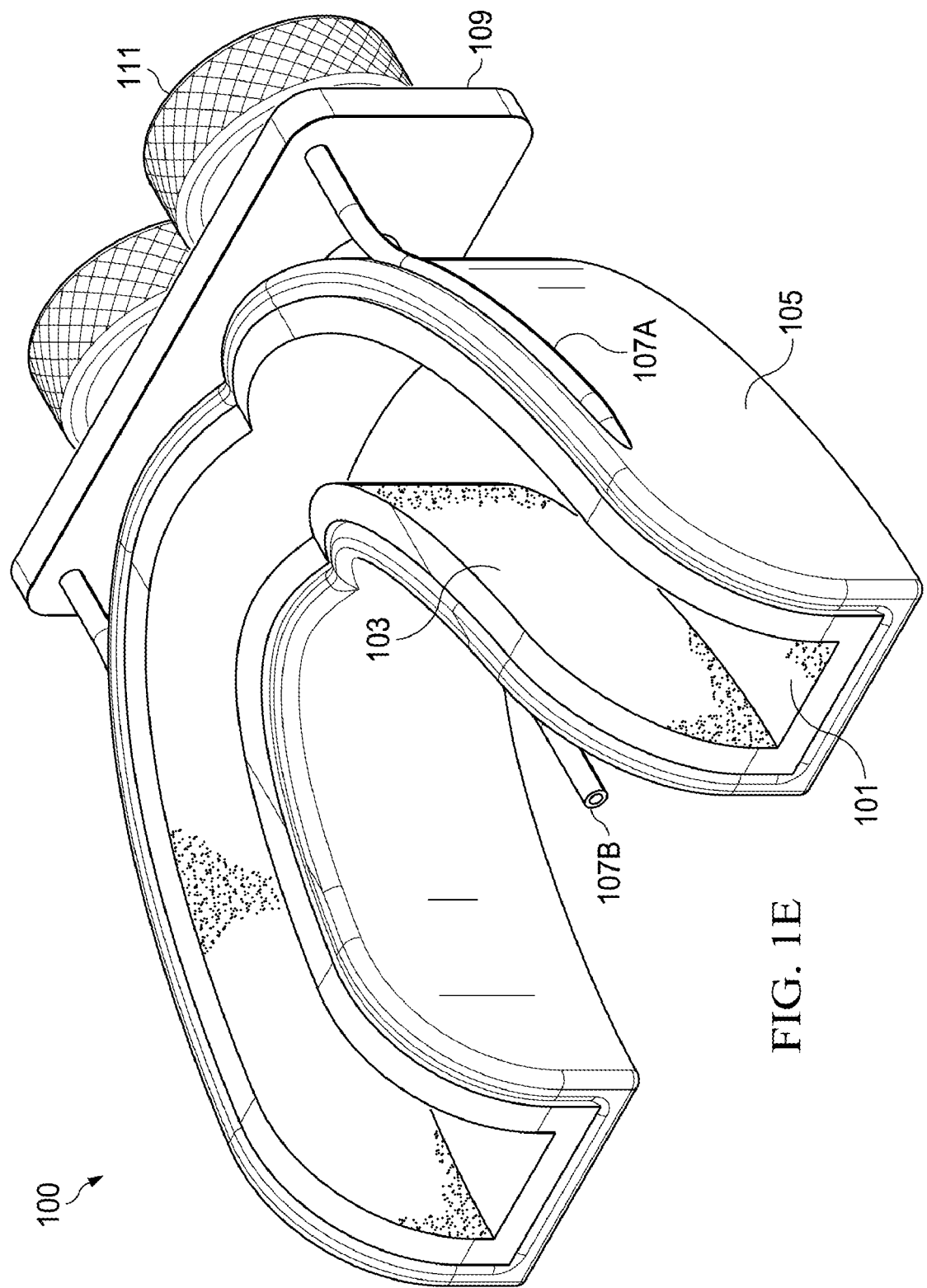
FIG. 1E shows a perspective view of an alternate embodiment of FIG. 1A, lacking the lingual area and lingual sensors.
Figure 2B:
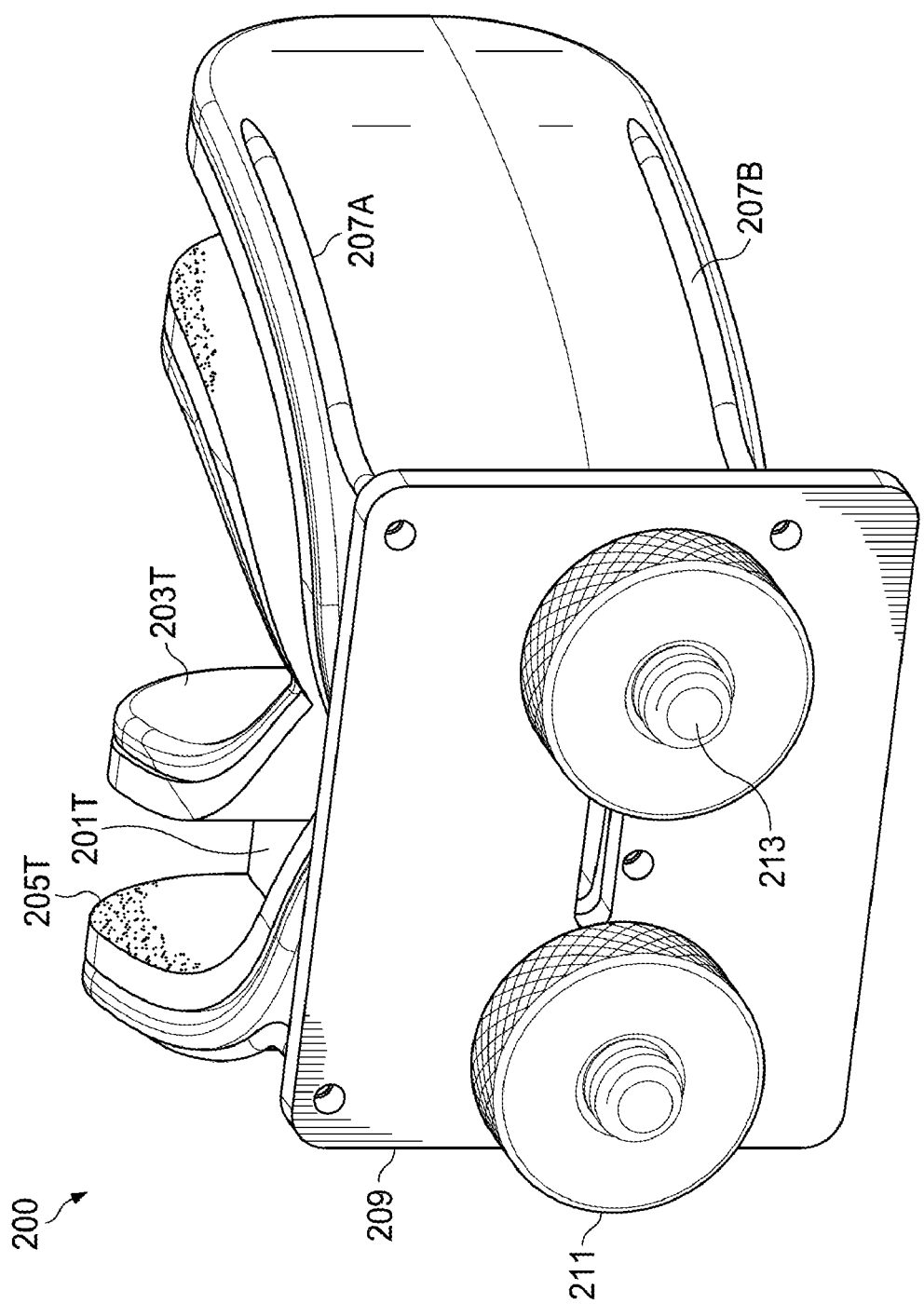
FIG. 2B shows a perspective view of FIG. 2A from the extraoral side.
Figure 2C:
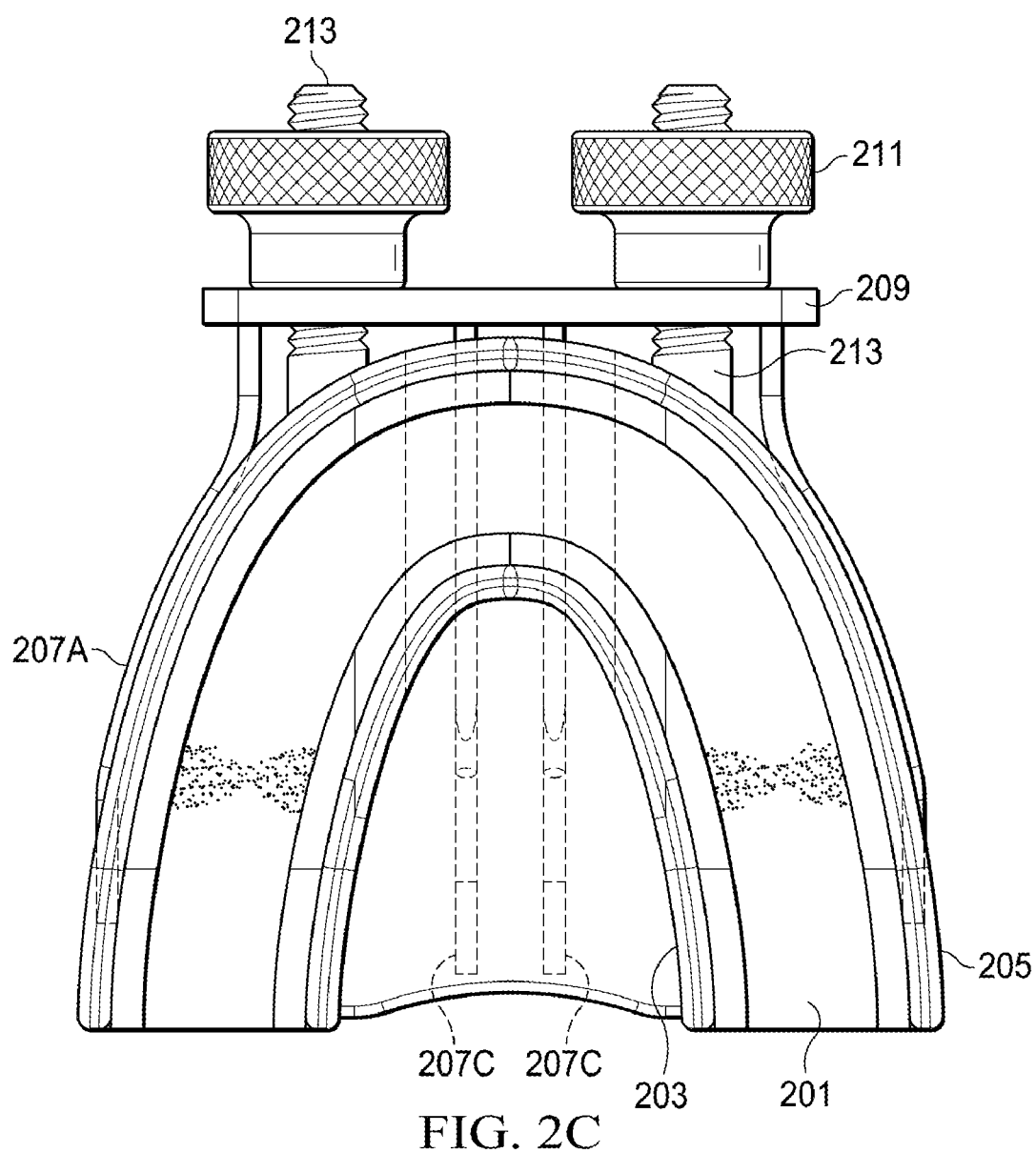
FIG. 2C is a top view of FIG. 2A.

FIG. 1E shows the device of FIG. 1A, but lacking the lingual area 108.

FIG. 2A-D is a dual arch sensor-containing mouthpiece 200. It is similar to the single arch design, but has upper and lower rims so that both arches (maxillary and mandibular) can be monitored at the same time with PSD sensors.

With references to FIG. 2A-D, the U-shaped base 201 allows contact with the occlusal surfaces of teeth, and rims or edges contact teeth. The buccal surfaces are contacted by upper outer rim 205T and lower outer rim 205B and the lingual surface by upper inner rim 203T and lower inner rim 203B. Lingual area 208 allows one or more sensors to be placed lingually to measure radiation at the tongue. The U-shaped base 201 has an extraoral component 209, having screw 213 and nut 211, however, other connectors are possible.

Tubes 207A, 207B, 207C and 207D provide conduits for the PSD sensors to be housed, thus allowing real-time radiation monitoring of radiation to the mouth, tongue and jaw area. Paired sensors 207A on the upper buccal rims 205T, paired sensors 207B on the lower buccal rims 205B, paired sensors under the mouthpiece 207C, and paired sensors 207D inside the lingual area 208. This arrangement of sensors is exemplary only, and other arrangements are possible.

Figure 3B:
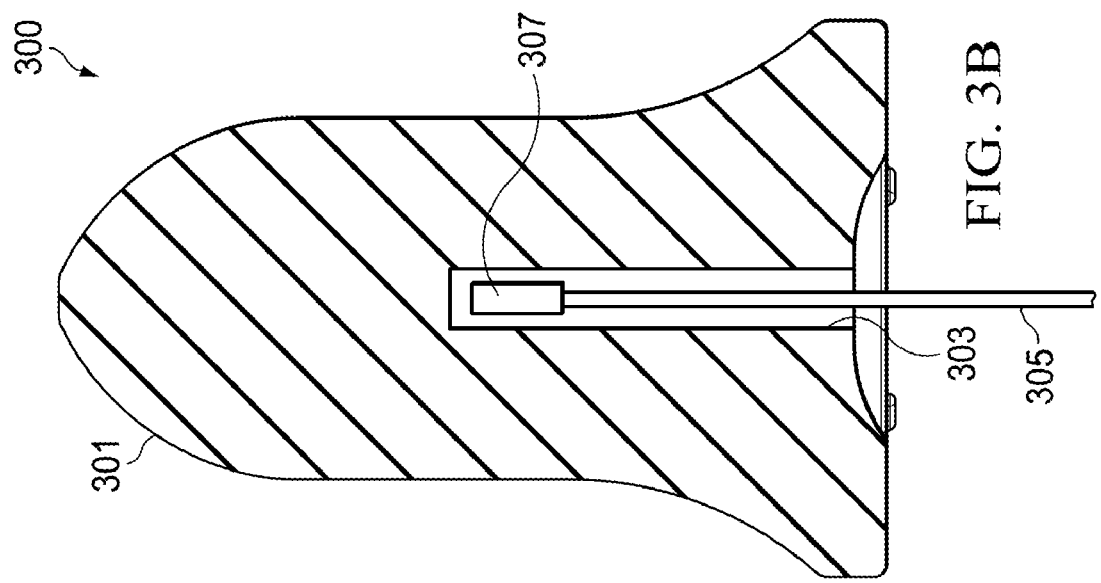
FIG. 3B is a cross section of the device of FIG. 3A through line A-A.
Figure 3A:
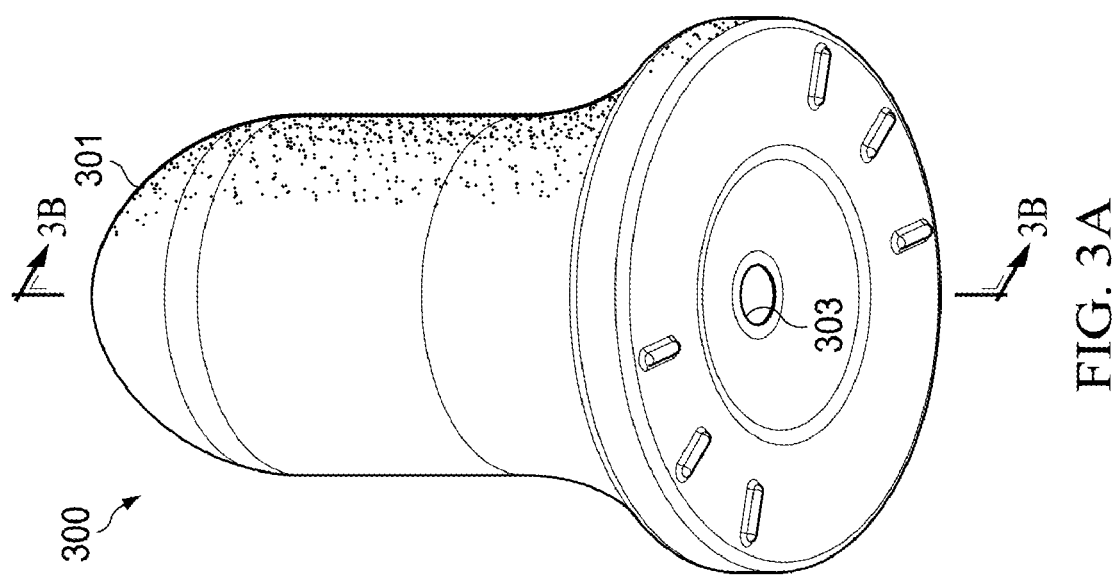
FIG. 3A is a perspective view of a nosepiece embodiment.

FIG. 3A-B shows a sensor-containing nosepiece embodiment 300 having a conical head 301 that is sized and shaped to fit an human nostril, and can be made available in a range of sizes (S, M, L, XL). The cone is gently rounded for comfort, and flared proximately to prevent accidental ingress. Blind conduit 303 holds sensor 305 with PSD 307 at the tip. Note that the tip 307 is shown somewhat larger, but this is for clarity only and it is usually minimally larger or the same diameter as the rest of the PSD cable.

Figure 4C:
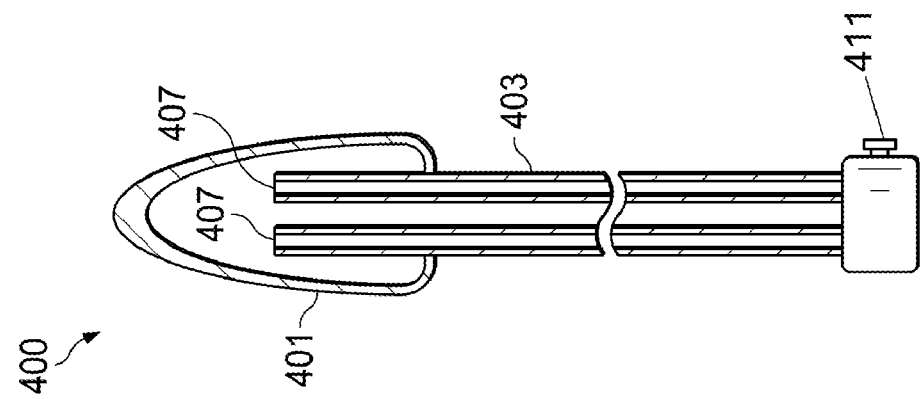
FIG. 4C is a cross section of the device of FIG. 4A through line A-A.
Figure 4B:
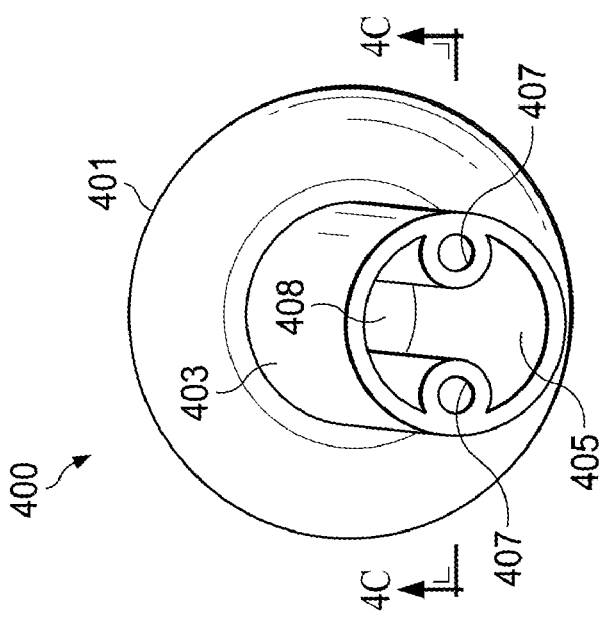
FIG. 4B is a perspective view of a 4A from the bottom, looking up at sensor conduits.
Figure 4A:
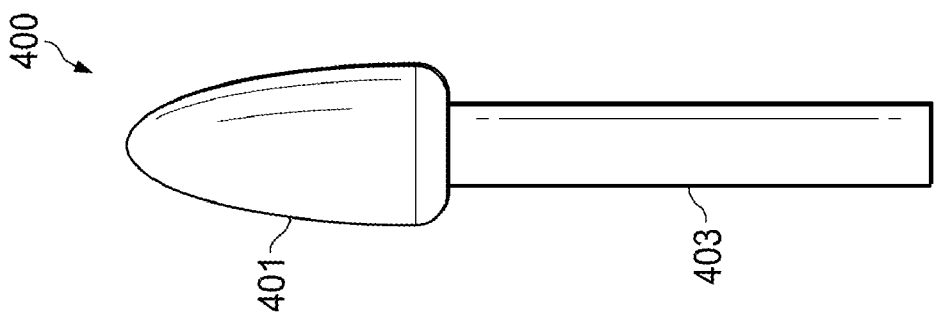
FIG. 4A is a side view of another nosepiece embodiment.

Rather than providing a range of sizes, FIG. 4A-C shows a sensor nosepiece or earpiece 400 that is inflatable. Cone 401 is attached to lumen or tube or hollow cylinder 403. Cone 401 is made of a semi-compliant or compliant polymeric film that can be inflated, thus fitting any human nostril. Cylinder 403 has at least two conduits—407 for the sensor (s) and 408 for inflation of cone 401. The inflation conduit 408 is fluidly connected to an interior of cone 401 such that the interior can be inflated. The other end of conduit 408 has a luer lock 411 or other valve means to control fluid ingress and egress. Conduits 407, herein shown a pair of conduits, can be closed, such that no air escapes therethrough. Here we show the distal end of conduits 407 closed (e.g., bind conduits), but other options are possible.

Figure 5C:
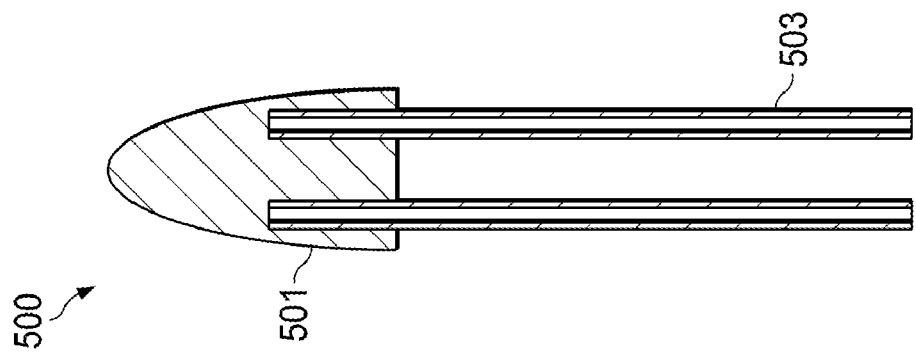
FIG. 5C is a cross section of the device of FIG. 5A through line A-A.
Figure 5B:
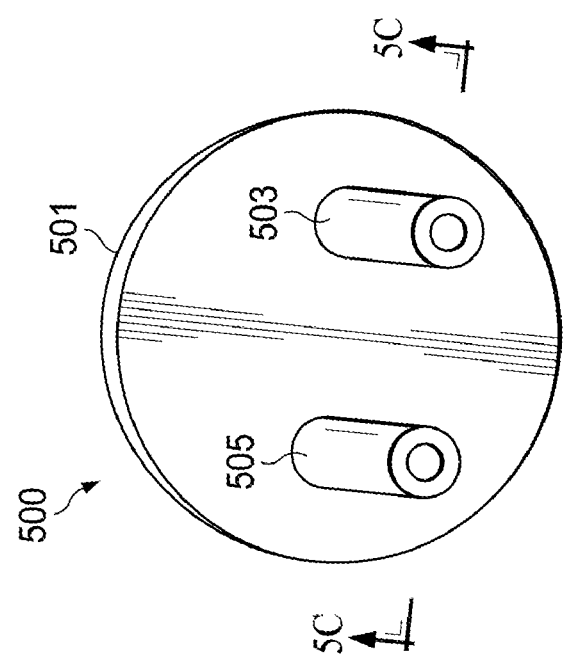
FIG. 5B is a perspective view of FIG. 5A from the bottom, looking up at sensor conduits.
Figure 5A:
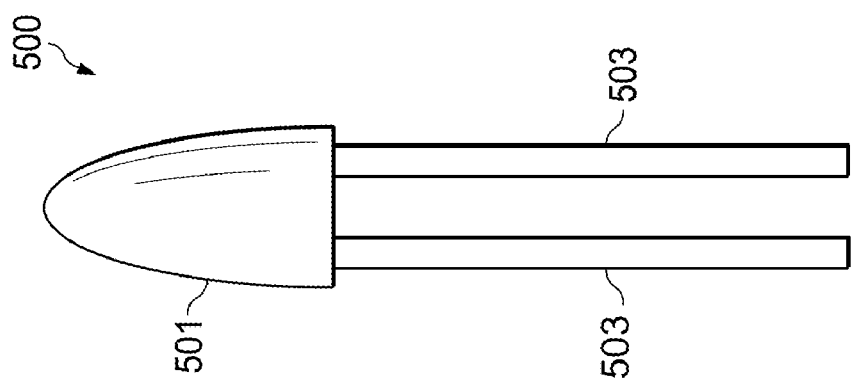
FIG. 5A is a side view of another nosepiece embodiment.
Figure 8A:
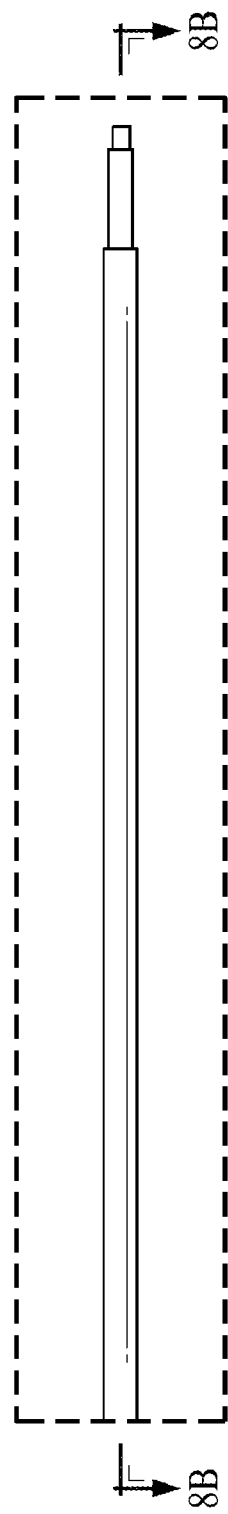
FIG. 8A-B are enlargement views of area B of sensor end of PSD cable.
Figure 8B:
Figure 9:
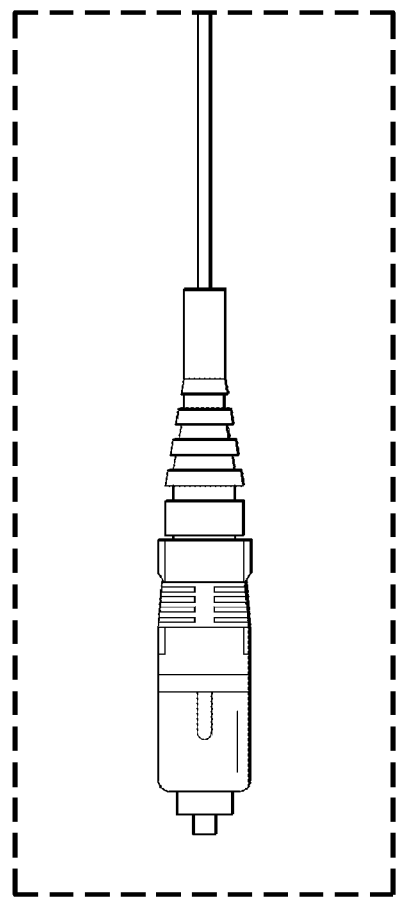
FIG. 9 enlargement view C of SC connector end of PSD cable.

FIG. 5A-C shows yet another sensor nose or ear embodiment, wherein cone 501 is made of soft flexible foam, such as is used in earplugs. Since the foam is very malleable, this device can be used for nostrils or ears. A pair of conduits 503 houses the PSD sensors (not shown), but the number and placement of conduits 503 can vary.

FIG. 6-9 show the cable as assembled by one possible method. In these figures, 1 is the scintillator fiber that has been dipped in a tantalum bath. A preferred scintillator fiber is a 0.5 mm BCF-60 by St Gobain with emission at 530 nm.

The plastic optic fiber or "POF" 2 is a Mitsubishi ESKA, POF Simplex, 0.5 mm core with opaque jacket, but other POFs may be suitable. Polymer optical fiber has a concentric double-layer structure with high-purity polymethyl methacrylate (known as PMMA) core and specially selected transparent fluorine polymer cladding. The cladding has a lower refractive index than that of the core. This special structure efficiently retains the light power inside the cable.

POF 2 is connected to the scintillator fiber 1 via epoxy 4, and supported in close juxtaposition by tube 7. Here we have used a polyimide tube, but any suitable tube could be used.

In order to assemble these components, the POF 2 jacket is stripped at the end, leaving a 0.5-1.5 inch segment of naked POF fiber 2B. Tube 7 is then fit over this naked end.

Next, about 0.1-1 μl, preferably about 0.2 μl of epoxy is placed on the sides of scintillator, and the cut scintillator fiber also inserted into the tube, gently guiding it to come to rest against the cut POF end. Any optically transparent epoxy can be used, but we have selected EPO-TEK® 301, a low viscosity, low temperature cured (65° C./1 hour), optically clear, two component epoxy adhesive. This adhesive previously passing the standard ISO10993 testing, has now successfully passed the more extensive testing of 12 weeks implantation.

Typically a small amount (0.5-2 mm) of scintillator fiber protrudes from the end of the tube, but this is not essential and is a matter of convenience of assembly.

Once the senor end is assembled, it is dipped into an opaque polymeric material to block light. Preferably this material also provides some strength or stiffening, and as such acts to protect the delicate sensor tip.

Connector 6 is added to the proximal end of the POF cable by known means. We have selected an SC connector (SFP-WDM-155M-20A LC by Elpa), which has a data rate of 100/155 Mbit/s, wavelength 1480-1580 nm, peak at 1310 nm, a sensitivity of −28 dBm, and power output −14 dBm minimum to −8 dBm maximum, with an input maximum at −8 dBm. However, there are many suitable connectors and the connector will vary with the photodetector employed to read the signal.

If the POF core is 0.5 mm, the whole cable must be at least 0.6 mm with the various coatings thereon, but can be as much as 1 mm. It is still small enough, however, to be used in in vivo applications, even on a urinary catheter, which is quite small.

Any suitable photodetector can be used with the above sensor, including those base on silicon photomultipliers (SiPMs), photomultiplier tubes, PIN photodiodes, multicolor cameras, monochromatic cameras, avalanche photodiode (APD); charge-coupled devices (CCD), and the like. Selection may vary with the application—the PIN, APD and PMT have higher sensitivity, suitable for low dose rate and out-of-field dose monitoring. PMT's relative uncertainty remains under 1% at the lowest dose rate achievable (50 μGy/s), suggesting optimal use for live dosimetry. For dose rate above 3 mGy/s, the PIN diode is the most effective photodetector in term of performance/cost ratio. For lower dose rate, such as those seen in interventional radiology, PMTs are the optimal choice. See also Ser. No. 15/135,576, filed Apr. 22, 2016, and 62/150,852, filed Apr. 22, 2015, entitled "MONOLITHIC PHOTODIODE DETECTOR FOR DOSIMETER."

Figure 10:
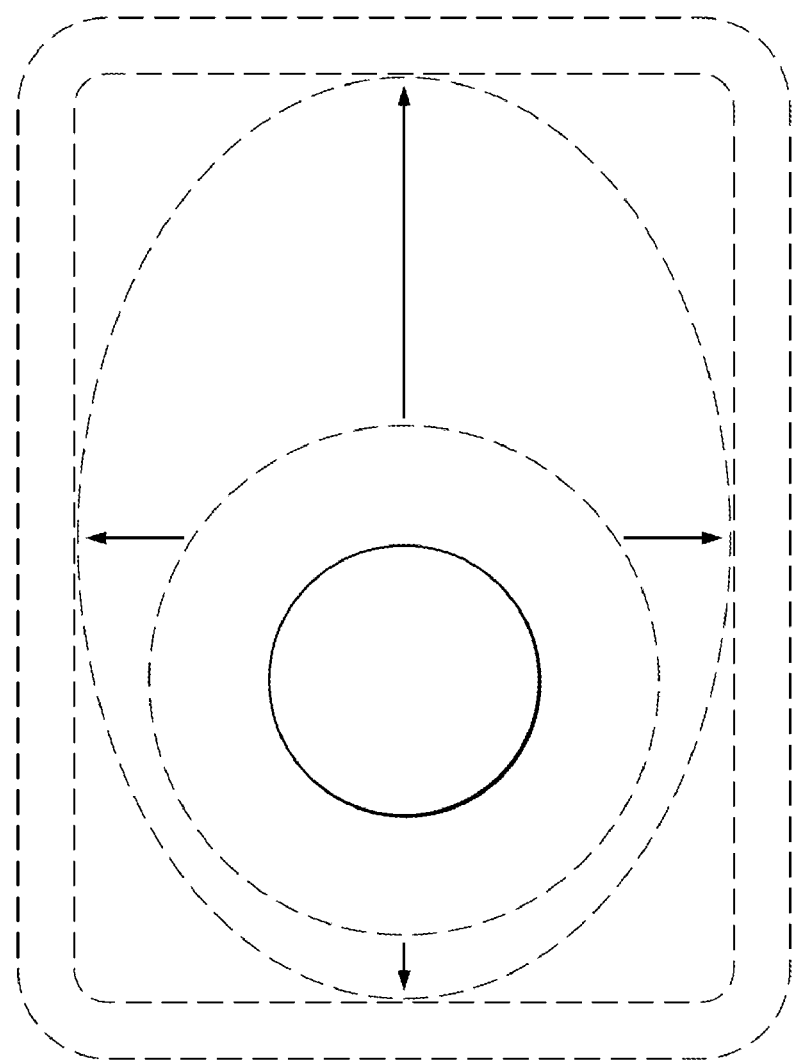
FIG. 10 Dosing graphic.

In use, a plan of the optimal distribution of the radiation sources is developed by the treating radiologist, and by using the sensor containing embodiments of the invention, the dose can be more accurately monitored, and hopefully the device and sensor usage will allow the use of smaller treatment volumes (FIG. 10).

FIG. 11-15 show completed prototypes without the sensors therein, wherein the hollow tubes extend proximally beyond the body of each device (11207, 12207, 13207, 14207, 150207), and each terminates in an adaptor (11200, 12200, 13200, 14200, 150200), that allows the sensor to be locked in place inside the hollow tube, herein shown Tuohy adaptors, but other valves could be used, such as luer locks, clamps, etc. Parts that are not labeled in these figures, are seen and discussed in the figures above.

Figures 13A, 13B:
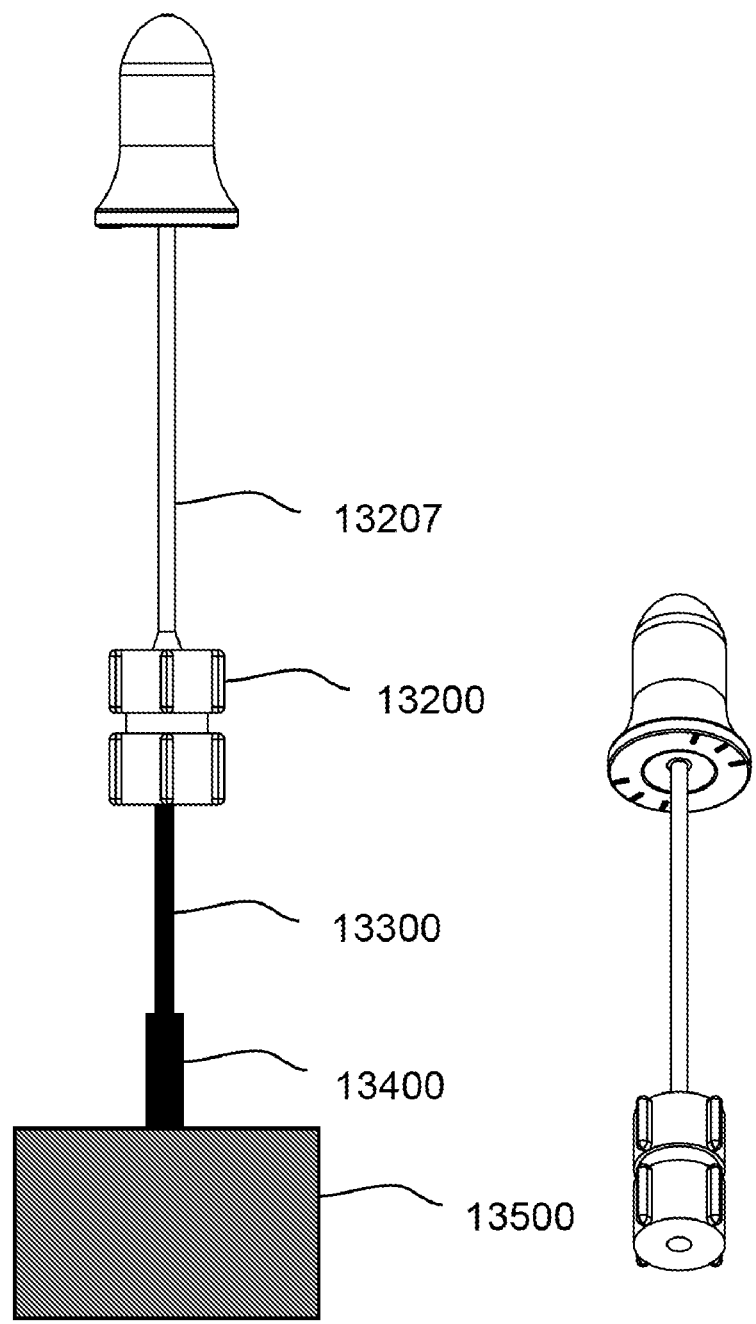
Figure 14A:
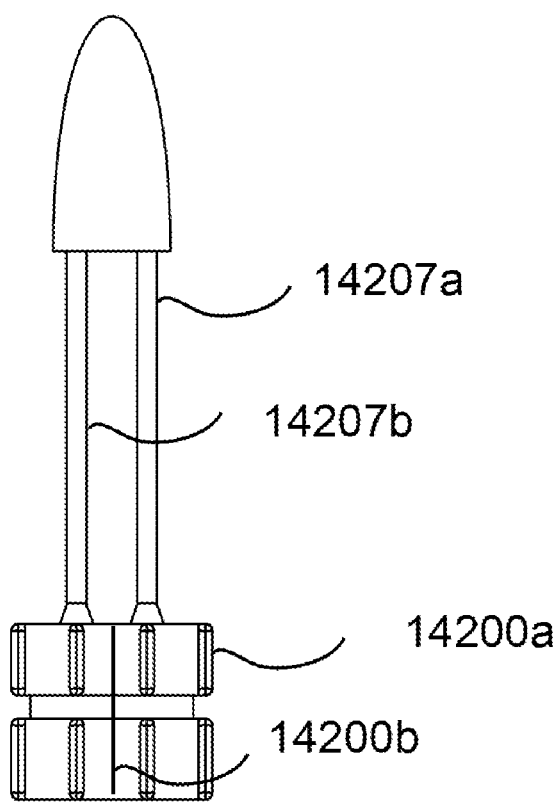
FIG. 14A top view of dual sensor nose or earpiece, 14B perspective and 14C end views.
Figure 14B:
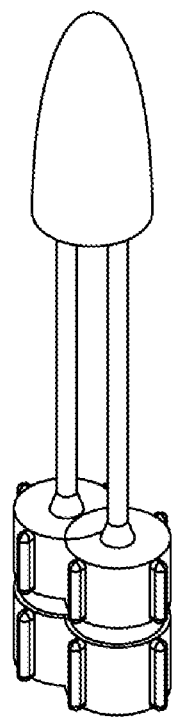
Figure 14C:
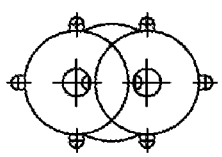
Figure 15A:
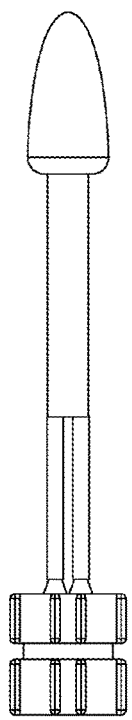
FIG. 15A depicts a top view of another embodiment of a dual sensor nose or earpiece.
Figure 15B:
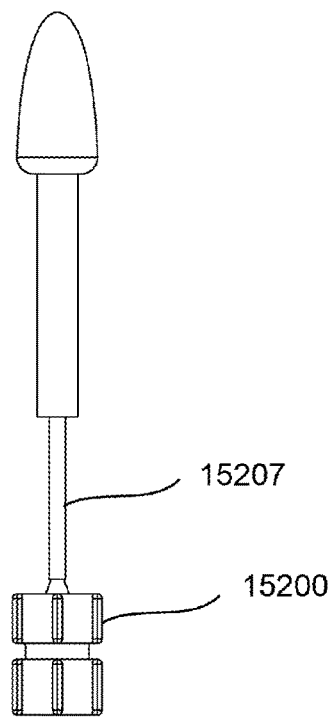
FIG. 15B depicts a side view of the embodiment of FIG. 15A.
Figure 15C:
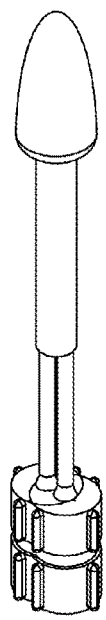
FIG. 15C depicts a perspective view of the embodiment of FIG. 15A.
Figure 15D:
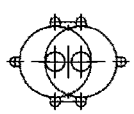
FIG. 15D depicts an end view of the embodiment of FIG. 15A.

FIG. 13A also shows the PSD sensor cable 13300 inserted into the hollow tube 13207 and having its own adaptor 13400, e.g., SMA adaptor, for connecting to a photodetector 13500.

In use the patient is prepped, the sensors loaded into the sensor conduits and the Tuohy tightened to lock the sensor in place. The sensor devices are then placed orally, nasally or aurally, as appropriate. For those devices that are inflatable, the next step is inflation to the desired level. The proximal end of the sensor cable is then connected to a photodetector. Although the devices could be integral, separate devices allow the cables to be changed when damaged.

If the sensor device or PSD tip is coated with e.g., tantalum or has any radio-opaque markers thereon, it can be imaged before treatment, to ensure reproducible positioning over the course of treatment, and if needed the device position can be adjusted. Position should also be recorded for use in the next treatment session. Once correctly positioned, the PSD cables that protrude from the device can be held in place against the skin using e.g., adhesive tape or clamps to prevent them from moving. If desired, further imaging can be performed to guide detailed treatment planning.

The images of the patient with the applicators in situ are imported into treatment planning software. The treatment planning software enables multiple 2D images of the treatment site to be translated into a 3D 'virtual patient', within which the position of the sensors can be defined. The spatial relationships between the treatment site and the surrounding healthy tissues within this 'virtual patient' are a copy of the relationships in the actual patient.

To identify the optimal distribution of radiation beams or radiation sources, the treatment planning software allows virtual radiation to be placed within the virtual patient. The software shows a graphical representation of the distribution of the irradiation. This serves as a guide for the radiotherapy team to refine the distribution of the beams or sources and provide a treatment plan that is optimally tailored to the anatomy of each patient before actual delivery of the irradiation begins. This approach is sometimes called 'dose-painting'. Herein, dose painting can be greatly improved with real-time feedback about delivered radiation.

Once the patient prepped, sensor in place, and imaging completed, treatment can commence, and dosimetry can be measured on a real-time basis at targeted locations via the PSD sensors within the applicator. Adjustments to positioning and/or total dosage or delivery rates can be made based on this real-time feedback, and the adjustments can be applied immediately, or in the next treatment session, as appropriate. Once the desired dosage level is reached for a given treatment session, the treatment is stopped. This can be repeated as often as necessary to target the tumor.

On completion of delivery of the radiation in a given session, the devices are disconnected from the photodetector. The balloon (if any) is deflated, and the device is carefully removed from the body. Patients typically recover quickly from the procedure, enabling it to often be performed on an outpatient basis.

The term "distal" as used herein is the end of the device inserted into the body cavity, while "proximal" is opposite thereto and is closest to the medical practitioner deploying the device. The terms top and bottom are in reference to the figures only, and do not necessarily imply an orientation on usage. The length of applicator plus handle and cables is the longitudinal axis, while a horizontal axis and vertical axis cross the longitudinal axis, and the cross sections are shown across the longitudinal axis.

As used herein the "GTV" or gross tumor volume is what can be seen, palpated or imaged.

As used herein "CTV" or "Clinical Target Volume" is the visible (imaged) or palpable tumor plus any margin of subclinical disease that needs to be eliminated through the treatment planning and delivery process.

The third volume, the "planning target volume" or "PTV", allows for uncertainties in planning or treatment delivery. It is a geometric concept designed to ensure that the radiotherapy dose is actually delivered to the CTV.

Radiotherapy planning must always consider critical normal tissue structures, known as organs at risk ("OAR"). In some specific circumstances, it is necessary to add a margin analogous to the PTV margin around an OAR to ensure that the organ cannot receive a higher-than-safe dose; this gives a planning organ at risk volume.

As used herein, a "cold spot" is a decrease of dose to an area significantly under the prescribed dose. While there is no hard fast rule as to what quantifies a cold spot, numbers greater than 10% below prescription should be scrutinized. A "hot spot" is the opposite, an area receiving >10% over prescription.

As used herein, "fractionation" refers to radiation therapy treatments given in daily fractions (segments) over an extended period of time, sometimes up to 6 to 8 weeks.

By "inflation" herein what is mean is inflation to the recommended pressure level, thus the volume will vary according to the size of the device, but typically range from 4-7 cc, or about for a nostril balloon, and 1-3 for an ear balloon.

By "radio-opaque" what is meant is a material that obstructs the passage of radiant energy, such as x-rays, the representative areas appearing light or white on the exposed film. In preferred embodiments, the devices are asymmetrically marked with a radio-opaque material such that placement and orientation can be reproducibly achieved with every treatment.

By "summation shadow" what is meant is when parts of a patient or an object in different planes are superimposed. The result is a summation image representing the degree of X-Ray absorption by all the superimposed objects. Radiolucent summation shadows are formed in the 'Swiss cheese' effect. Radiopaque summation shadows are involved in the 'bunch of grapes' effect.

By "silhouette effect" what is meant is the fact that when two structures of the same radiopacity are in contact, their individual margins at the point of contact cannot be distinguished. One is said to silhouette with the other, or to form a positive silhouette sign.

By "blind" tube, we mean that one end (usually the distal end inside the device) is closed, such that air cannot escape through said hollow tube.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim. The term "consisting of" is a closed linking verb, and does not allow the addition of other elements.

The term "consisting essentially of" occupies a middle ground, allowing non-material elements to be added. In this case, these would be elements such as marking indicia, radio-opaque markers, a stopper, packaging, instructions for use, labels, and the like.

The following abbreviations may be used herein:

| | |
|---|---|
| ABS | Acrylonitrile butadiene styrene |
| ADP | Avalanche photodiode |
| APBI | Accelerated partial breast irradiation |
| CCD | Charge-coupled devices |
| CRT | Conformal radiation therapy |
| CT | Computer tomography |
| CTV | Clinical Target Volume. |
| DVH | Dose-volume histogram |
| EBRT | External beam radiation therapy, sometimes XRT |
| GTV | Gross tumor volume |
| HDR | High dosage rate |
| IGRT | Image guided radio therapy |
| IMRT | Intensity-modulated radiation therapy |
| IV | Irradiated volume |
| LDR | Low dosage rate |
| MPPC | Multipixel photon counter |
| MRI | magnetic resonance imaging |
| OAR | Organ at risk |
| PCB | Printed circuit board |
| PDR | Pulsed dosage rate |
| PEEK | Polyether ether ketone |
| PET | position emission tomography or polyethylene terephthalate |
| PIN | P-type semiconductor-intrinsic semiconductor-n-type semiconductor region. PIN diode is a diode with a wide, undoped intrinsic semiconductor region between a p-type semiconductor and an n-type semiconductor region. |
| PMT | Photomultiplier tubes (photomultipliers for short), vacuum phototubes are extremely sensitive detectors of light in the ultraviolet, visible, and near-infrared ranges of the electromagnetic spectrum. These detectors multiply the current produced by incident light by as much as 100 million times (i.e., 160 dB), in multiple dynode stages, enabling (for example) individual photons to be detected when the incident flux of light is low. |
| POF | Plastic optic fiber |
| PRV | Planning organ-at-risk volume |
| PTV | Planning target volume |
| PVC | Poly vinyl chloride |
| RVR | Remaining volume at risk |
| SiPM | Silicon photomultiplier, see also MPPC |
| TV | Treated volume |
| XRT | radiation therapy |

The foregoing disclosure and description of the invention are illustrative and explanatory thereof, and various changes in the details of the illustrated apparatus and system, and the construction and method of operation may be made without departing from the spirit of the invention.

Each of the following is incorporated by reference herein in its entirety for all purposes:

Boivin, J. et al., Systematic evaluation of photodetector performance for plastic scintillation dosimetry, Med. Phys. 42(11): 6211-6220 (2015).

Lessard, F., et al., Validating plastic scintillation detectors for photon dosimetry in the radiologic energy range, Med Phys. 39(9): 5308-5316 (2012).

Wootton L. & Beddar, S., Temperature dependence of BCF plastic scintillation detectors, Phys Med Biol. 58(9): 10.1088/0031-9155/58/9/2955 (2013).

US20140221724, US20140221724, U.S. Pat. No. 8,735,828 "REAL-TIME IN VIVO RADIATION DOSIMETRY USING SCINTILLATION DETECTOR" by Beddar Ser. No. 15/135,576, filed Apr. 22, 2016, and 62/150,852, filed Apr. 22, 2015, entitled "MONOLITHIC PHOTO-DIODE DETECTOR FOR DOSIMETER"

US20100288934, US20140018675, US20150216491, U.S. Pat. Nos. 9,028,390, 9,351,691, "APPARATUS AND

METHOD FOR EXTERNAL BEAM RADIATION DISTRIBUTION MAPPING" by Keppel
US20060173233 "BRACHYTHERAPY APPLICATOR FOR DELIVERY AND ASSESSMENT OF LOW-LEVEL IONIZING RADIATION THERAPY AND METHODS OF USE" by Lovoi
WO2003062855 "METHOD AND APPARATUS FOR REAL TIME DOSIMETRY" by Rosenfeld
US20100318029 "SEMI-COMPLIANT MEDICAL BALLOON"
U.S. Pat. No. 4,584,991 "MEDICAL DEVICE FOR APPLYING THERAPEUTIC RADIATION"
US20150335913 "BRACHYTHERAPY APPLICATOR DEVICE FOR INSERTION IN A BODY CAVITY"
61/481,503, filed May 2, 2011, Ser. No. 13/444,584 (now U.S. Pat. No. 8,885,986), filed Apr. 11, 2012, Ser. No. 14/470,707 (now U.S. Pat. No. 8,953,912), filed Aug. 27, 2014 "SMALL DIAMETER RADIATION SENSOR CABLE"
62/049,258, filed Sep. 11, 2014, and Ser. No. 14/849,790 (pending), "SKIN PATCH DOSIMETER"
62/063,196 filed Oct. 13, 2014, Ser. No. 14/881,023, filed on Oct. 12, 2015 (pending); "URINARY RADIATION SENSOR CATHETER"

What is claimed:

1. A device comprising:
a bite plate comprising a housing and at least one conduit within the housing; wherein the bite plate housing is configured to be shaped to fit in a human mouth; and
at least one scintillating radiation sensor cable; wherein the at least one scintillating radiation sensor cable is configured to be placed within the conduit.

2. The device of claim 1, wherein the bite plate housing further comprises a substantially U-shaped base.

3. The device of claim 2, wherein the bite plate housing further comprises at least one outer rim.

4. The device of claim 3, wherein the bite plate housing further comprises a lingual portion.

5. The device of claim 4, wherein the at least one conduit may extend within one of the following: the substantially U-shaped base; the at least one outer rim; or the lingual portion.

6. The device of claim 1, wherein the bite plate further comprises an extraoral base.

7. The device of claim 6, wherein the extraoral base is configured to be connected to a radiation mask.

8. The device of claim 1, wherein the at least one scintillating radiation sensor cable comprises a diameter up to 1 mm.

9. The device of claim 8, wherein the at least one scintillating radiation sensor cable is configured for real-time radiation monitoring.

10. A device comprising:
a cone comprising a housing and at least one conduit within the housing; wherein the cone housing is configured to be shaped to fit in a human nose or ear; and
at least one scintillating radiation sensor cable; wherein the at least one scintillating radiation sensor cable is configured to be placed within the conduit.

11. The device of claim 10, wherein the cone housing is inflatable.

12. The device of claim 11, wherein the cone further comprises an inflation lumen.

13. The device of claim 10, wherein the cone housing is comprised of a compressible foam material.

14. The device of claim 10, wherein the cone housing further comprises a distal end and a proximal end and is configured to flare from the distal end towards the proximal end.

15. The device of claim 10, wherein the at least one scintillating radiation sensor cable is configured for real-time radiation monitoring.

16. A device comprising:
a housing and at least one conduit within the housing; wherein the housing is configured to be shaped to fit in any of the following human orifices: a mouth, a nose, or an ear; and
at least one scintillating radiation sensor cable; wherein the at least one scintillating radiation sensor cable is configured to be placed within the conduit.

17. The device of claim 16, wherein the housing further comprises a substantially U-shaped bite plate.

18. The device of claim 16, wherein the housing further comprises an inflatable element.

19. The device of claim 16, wherein the housing further comprises a foam plug.

20. The device of claim 16, wherein the at least one scintillating radiation sensor cable is configured for real-time radiation monitoring.

* * * * *